United States Patent
Chiou et al.

(10) Patent No.: US 9,770,721 B2
(45) Date of Patent: Sep. 26, 2017

(54) CONTINUOUS WHOLE-CHIP 3-DIMENSIONAL DEP CELL SORTER AND RELATED FABRICATION METHOD

(71) Applicant: The Regents Of The University Of California, Oakland, CA (US)

(72) Inventors: Pei-yu E. Chiou, Los Angeles, CA (US); Kuo-wei Huang, Hillsboro, OR (US); Yu-jui Fan, Taipei (TW); Yu-chun Kung, Los Angeles, CA (US)

(73) Assignee: The Regents of the University of California, Oakland, CA (US)

( * ) Notice: Subject to any disclaimer, the term of this patent is extended or adjusted under 35 U.S.C. 154(b) by 426 days.

(21) Appl. No.: 14/388,212

(22) PCT Filed: Mar. 27, 2013

(86) PCT No.: PCT/US2013/034145
§ 371 (c)(1),
(2) Date: Sep. 25, 2014

(87) PCT Pub. No.: WO2013/148865
PCT Pub. Date: Oct. 3, 2013

(65) Prior Publication Data
US 2015/0041325 A1 Feb. 12, 2015

Related U.S. Application Data

(60) Provisional application No. 61/616,385, filed on Mar. 27, 2012, provisional application No. 61/799,451, filed on Mar. 15, 2013.

(51) Int. Cl.
*G01N 27/453* (2006.01)
*B03C 5/00* (2006.01)
(Continued)

(52) U.S. Cl.
CPC ........ *B03C 5/005* (2013.01); *B01L 3/502761* (2013.01); *B03C 5/026* (2013.01);
(Continued)

(58) Field of Classification Search
CPC ............................................ B03C 5/00–5/028
See application file for complete search history.

(56) References Cited

U.S. PATENT DOCUMENTS

| 6,149,789 A | 11/2000 | Benecke et al. |
| 6,730,204 B2 | 5/2004 | Mariella, Jr. |

(Continued)

FOREIGN PATENT DOCUMENTS

| CN | 104321126 | 1/2015 |
| EP | 2830740 | 2/2015 |

(Continued)

OTHER PUBLICATIONS

Chinese First Office Action dated Sep. 6, 2015 issued in CN 2013800281189.

(Continued)

*Primary Examiner* — Alexander Noguerola
(74) *Attorney, Agent, or Firm* — Weaver Austin Villeneuve & Sampson LLP

(57) ABSTRACT

A 3-dimensional PDMS cell sorter having multiple passages in a PDMS layer that follow the same path in a DEP separation region and that are in fluid communication with each other within that region. The passages may differ in width transverse to the flow direction within the passages. Flat plates may sandwich the PDMS layer; each plate may have a planar electrode used to generate a DEP field within a sample fluid flowed within the passages. The DEP field may concentrate target cells or particulates within one of the passages within the DEP separation region. The passages may diverge after the DEP-separation region, leaving one (Continued)

passage with a high concentration of target cells or particulates. Techniques for manufacturing such structures, as well as other micro-fluidic structures, are also provided.

28 Claims, 16 Drawing Sheets

(51) Int. Cl.
    *G01N 27/447* (2006.01)
    *B03C 5/02* (2006.01)
    *G01N 15/06* (2006.01)
    *B01L 3/00* (2006.01)
    *G01N 15/00* (2006.01)
    *G01N 15/10* (2006.01)

(52) U.S. Cl.
    CPC ... *G01N 15/0656* (2013.01); *G01N 27/44778* (2013.01); *B01L 2200/0652* (2013.01); *B01L 2300/0816* (2013.01); *B01L 2300/0864* (2013.01); *B01L 2300/0867* (2013.01); *B01L 2400/0424* (2013.01); *B01L 2400/0655* (2013.01); *B03C 2201/26* (2013.01); *G01N 2015/0065* (2013.01); *G01N 2015/1081* (2013.01)

(56) References Cited

U.S. PATENT DOCUMENTS

| | | | |
|---|---|---|---|
| 7,070,681 B2 | 7/2006 | Santiago et al. | |
| 7,686,934 B2 | 3/2010 | Hodko et al. | |
| 7,956,339 B2 | 6/2011 | Ohta et al. | |
| 2006/0073035 A1* | 4/2006 | Sundararajan | F04B 43/043 417/412 |
| 2006/0290745 A1* | 12/2006 | Feng | B03C 5/026 347/65 |

FOREIGN PATENT DOCUMENTS

| | | | |
|---|---|---|---|
| JP | 2011-185684 A | 9/2011 | |
| WO | 2007105784 A1 | 9/2007 | |
| WO | 2007138464 A2 | 12/2007 | |
| WO | 2007138464 A3 | 12/2007 | |
| WO | WO2013028058 A1 * | 2/2013 | B03C 5/02 |
| WO | 2013/148865 | 10/2013 | |

OTHER PUBLICATIONS

International Search Report and Written Opinion—PCT/US2013/034145—ISA/KR—Jul. 10, 2013.
International Preliminary Report on Patentability—PCT/US2013/034145, The International Bureau of WIPO—Geneva, Switzerland, Oct. 9, 2014.
Kung et al., "Fabrication of 3D Microfluidic Networks with a Hybrid Stamp," MEMS 2013. 4 pp., Jan. 20-24, 2013.
Chinese Second Office Action dated May 9, 2016, issued in CN 201380028118.9.
European Partial Search Report dated Nov. 4, 2015, issued in EP 13767786.0.
European Extended Search Report dated Mar. 11, 2016, issued in EP 13767786.0.
Japanese First Office Action dated Nov. 28, 2016, issued in JP 2015-503542.
Huang et al., "Electrodes for Microfluidic Integrated Optoelectronic Tweezers," Advances in OptoElectronics, 2011, 11 pgs.

* cited by examiner

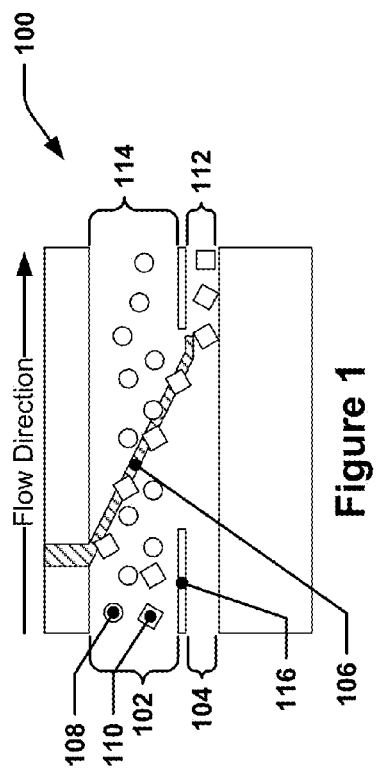
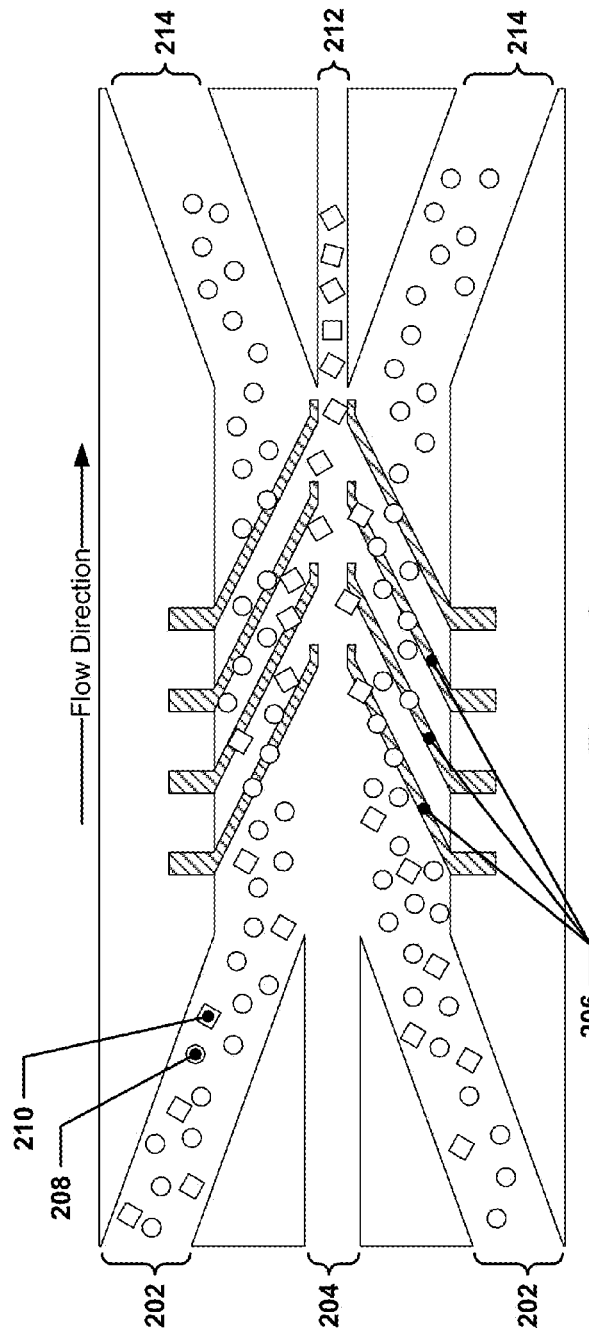
Figure 1
Figure 2

CONTINUOUS WHOLE-CHIP 3-DIMENSIONAL DEP CELL SORTER AND RELATED FABRICATION METHOD

CROSS REFERENCE TO RELATED APPLICATIONS

This application claims benefit under 35 U.S.C. §371 to PCT/US13/34145 filed on Mar. 27, 2013, and under 35 U.S.C. §119(e) to U.S. Provisional Application No. 61/616, 385, filed Mar. 27, 2012, titled "CONTINUOUS WHOLE-CHIP 3-DIMENSIONAL DEP CELL SORTER AND ITS FABRICATION", and U.S. Provisional Application No. 61/799,451, filed Mar. 15, 2013, titled "CONTINUOUS WHOLE-CHIP 3-DIMENSIONAL DEP CELL SORTER AND RELATED FABRICATION METHOD," both of which are hereby incorporated by reference herein in their entirety.

GOVERNMENT LICENSE RIGHTS

This invention was made with US Government support under Grant No. 0901154, awarded by the National Science Foundation. The US Government has certain rights in this invention.

BACKGROUND OF THE INVENTION

Microfluidic devices present a cost-effective mechanism for performing small-scale fluidic manipulation on various fluid-entrained samples. For example, some microfluidic devices may be used to route, sort, and analyze cells contained in a fluid sample.

Multilayer soft lithography (MSL) is by far the most widely used approach for fabricating microfluidic devices. Numerous devices, from simple monolayer polydimethylsiloxane (PDMS) channels to multilayer structures with pneumatically controlled pumps and valves, have been used to provide versatile microfluidic functions including liquid delivery, mixing, and metering. Microfluidic large-scale integration (mLSI) has been realized in the form of microfluidic multiplexers to individually address thousands of valves and hundreds of chambers for conducting complex and multistep biochemical analyses, e.g., in lab-on-a-chip devices. Most multilayer PDMS devices demonstrated so far are not true 3D microfluidic devices. Although multiple layers of 2D microfluidic networks can be stacked, there is typically no interlayer fluid communication due to the difficulty of fabricating high-resolution through-layer vias for fluidly connecting different layers in high yield. Without through-layer vias, fluid routing and interfacing become complex issues for large scale 3D microfluidic networks.

One function that microfluidic devices may provide is cell or particulate sorting. For example, a fluid sample may have a variety of different types of cells or particles entrained within, and it may be desirable to isolate or concentrate cells or particles of a particular type with respect to the overall sample. Dielectrophoresis (DEP) is one of the most commonly used mechanisms exploited to sort cells or particulates. DEP refers to induced particle motion along an electric field gradient due to the interactions between induced electric dipoles of the particles and the applied electric field. The DEP force acting on a spherical particle, FDEP, suspended in a medium may be expressed as:

$$\vec{F}_{DEP} = 2\pi \in_1 \text{Re}[K(\omega)] r^3 \nabla E^2$$

where r is the radius of the particle, K is the Clausius-Mossotti factor, E is the electric field strength, ω is the angular frequency of the applied field, and $\in_1$ is the dielectric permittivity of the media. Since the resultant force is dependent on the electric field intensity gradient, $\nabla E^2$, the particle can be attracted towards any inhomogeneities in the field, created for example by the metallic patches on micropatterned-templates. The sign and the effective polarizability of the spherical particle may be expressed as:

$$\text{Re}[K] = \frac{\varepsilon_2^* - \varepsilon_1^*}{\varepsilon_2^* + 2\varepsilon_1^*} \quad \varepsilon_1^* = \varepsilon_1 + \frac{\sigma_1}{j\omega} \quad \varepsilon_2^* = \varepsilon_2 + \frac{\sigma_2}{j\omega}$$

where $\sigma_1$ is the conductivity of the media and $\in_2$ and $\sigma_2$ dielectric permittivity and conductivity for the particles. If Re[K] is positive, particles move towards the strong electric field regions; in contrast, If Re[K] is negative, particles move to the low electric field regions.

Thus, a cell or particulate subjected to a non-uniform electric field experiences a force due to DEP effects. The magnitude of the force is dependent on various factors, including the dielectric signature of the cell or particulate, as well as the frequency of the electric field. Depending on the DEP field used and the characteristics of the individual cells or particulates subject to the DEP field, cells or particulates may experience either positive DEP (experiencing force that urges the cell or particulate in the direction of increasing field strength) or negative DEP (experiencing force that urges the cell or particulate in a direction opposite of increasing field strength). In many cases, the movement of cells or particulates via DEP may be practically limited to approximately 100 μm/s given the characteristics of those cells or particulates, the media that are commonly used to transport them, and the electrical characteristics of microfluidic systems.

DEP response of cells or particulates may be altered or enhanced by tagging cells or particulates of interest with molecules, e.g., labeled or unlabeled antibodies, or beads that are specific to certain cells or particulates of interest. This may allow for easier separation of the target cells or particulates using DEP. While such tagging can enhance DEP techniques, it is not necessary in many cases.

FIG. 1 depicts one example of a two-dimensional DEP cell sorter 100. FIG. 1 shows only a plan view of a portion of a PDMS layer of the cell sorter 100; in actual practice, the PDMS layer would be sandwiched between two plates, e.g., glass plates, that are not shown. The PDMS layer may include a sample channel 102 and a buffer channel 104 that run parallel to one another and that are separated from one another by a thin wall 116. A fluid sample and a buffer may be flowed into the sorter from, with respect to the orientation of FIG. 1, left to right via their respective channels. The thin wall 116 may have an opening 118 that permits fluid communication between the sample channel 102 and the buffer channel 104. Patterned electrodes 106 may extend at an angle across the sample channel 102; a patterned electrode 106 may be patterned on each of the two plates. An electromagnetic field may be produced within the sample fluid that is flowed through the sample channel 102 between patterned electrodes 106 when an alternating current is used to produce a voltage across the electrodes. Depending on the frequency of the electromagnetic field, certain cells, e.g., "square" cells 110, may be drawn towards the maximum field strength and "round" cells 108 may be repulsed or unaffected. The angled nature of the electromagnetic field (due to the angle of the patterned electrodes 106) may cause the square cells 110 to be drawn towards the buffer channel 104 as the fluid flow in the sample channel 102 and the buffer channel 104 progresses, with respect to the orientation of FIG. 1, from left to right. After the end of the opening 118, the square cells 110 that have been shunted towards the buffer channel 104 may flow into a collection channel 112, whereas the round cells may flow into a waste channel 114.

FIG. 2 depicts another example of a two-dimensional DEP cell sorter 200. In this case, the cell sorter 200 includes two sample channels 202 that bracket a buffer channel 104. A fluid sample may be flowed into the cell sorter 200 via the sample channels 202 while a neutral buffer may be flowed into the cell sorter 200 via the buffer channel 204. The combined buffer/sample fluid flows through a sorting region containing a number of patterned electrodes 206. When the patterned electrodes 206 are powered at a particular frequency, the resulting electromagnetic field may cause the square cells 210 to migrate towards the center of the cell sorter 200, whereas the round cells 208 may migrate towards, or stay in, the outer edges of the cell sorter 200. The center-concentrated square cells 210 may then flow into a collection channel 212, whereas the round cells 208 may flow into waste channels 214.

Two-dimensional cell sorters typically have a maximum flow rate beyond which the cell sorting functionality is lost or significantly impaired. The forces produced by DEP, and consequently the rate at which DEP can move cells across the flow stream and into position for flow into the collection channels, are limited by the size and shape of the electrodes as well as other system characteristics. If the fluid flow rate is fast enough that the cells flow past the patterned electrodes before the forces produced by the DEP effect can re-position the cells for flow into the collection channels, then the cells will not be effectively sorted. This limits the maximum flow of two-dimensional cell sorters, and, consequently, the maximum throughput of a two-dimensional cell sorter. Such two-dimensional DEP cell sorters are thus typically limited to maximum flow rates of approximately 1 mm/sec, which, in turn, limits the throughput of such cell sorters.

SUMMARY

Details of one or more embodiments of the subject matter described in this specification are set forth in the accompanying drawings and the description below. Other features, aspects, and advantages will become apparent from the description, the drawings, and the claims. Note that the relative dimensions of the following figures may not be drawn to scale unless specifically indicated as being scaled drawings.

In various aspects, the invention(s) contemplated herein may include, but need not be limited to, any one or more of the following embodiments:

Embodiment 1: A 3-dimensional dielectrophoretic (DEP) sorting device, the device including: a first electrode; a second electrode; an electrically-insulating layer sandwiched between the first electrode and the second electrode, wherein: the electrically-insulating layer includes a separation passage with walls partially bounded by the first electrode and the second electrode, the electrically-insulating layer includes a collection passage smaller than the separation passage in cross-sectional thickness and located at an inter-electrode location between the first electrode and the second electrode, the separation passage is shaped to produce an electromagnetic field that causes a dielectrophoretic effect to draw responsive cells or particulates to a location between the first electrode and the second electrode that substantially corresponds with the inter-electrode location of the collection passage, and the collection passage and the separation passage are configured such that cells or particulates drawn to the inter-electrode location between the first electrode and the second electrode in the separation passage are then flowed into the collection passage.

Embodiment 2: A 3-dimensional dielectrophoretic (DEP) sorting device, the device including: a first electrode; a second electrode; an electrically-insulating layer sandwiched between the first electrode and the second electrode, wherein: the electrically-insulating layer includes: a fluid flow passage, the fluid flow passage having a cross-section partially defined by the first electrode and the second electrode; a first side passage that is parallel to the fluid flow passage within a DEP-separation region of the device and separated from the fluid flow passage by a first thin, deformable wall; a second side passage that is parallel to the fluid flow passage within the DEP-separation region and separated from the fluid flow passage by a second thin, deformable wall, wherein: the first side passage and the second side passage are hermetically sealed from the fluid flow passage, and application of pressurized gas or fluid to the first side passage and the second side passage causes the first thin, deformable wall and the second thin, deformable wall to bulge into the fluid flow passage.

Embodiment 3: The 3-dimensional DEP sorting device of embodiment 2, wherein drawing a vacuum on the first side passage and the second side passage causes the first thin, deformable wall and the second thin, deformable wall to bulge into the side passages.

Embodiment 4: The 3-dimensional DEP sorting device of embodiment 2 or embodiment 3, wherein the side passages are filled with a liquid or gel.

Embodiment 5: The 3-dimensional DEP sorting device of embodiment 4, wherein the liquid or gel is cured into a solid form after being pressurized, thus causing the thin, deformable walls to bulge into the fluid flow passage, or subjected to a vacuum, thus causing the thin, deformable walls to bulge into the side passages.

Embodiment 6: A 3-dimensional dielectrophoretic (DEP) sorting device, the device including: a first electrode layer; a second electrode layer; an electrically-insulating layer interposed between the first electrode layer and the second electrode layer and having a first sub-layer and a second sub-layer; a first passage located in the first sub-layer; and a second passage located in the second sub-layer; wherein: the first electrode layer, the second electrode layer, and the electrically-insulating layer form a substantially planar assembly, the first electrode layer is on an opposite side of the first sub-layer from the second layer, the second electrode layer is on an opposite side of the second sub-layer from the first layer, the first passage and the second passage follow a common path within a DEP separation region of the electrically-insulating layer and are in direct fluid communication with one another within the DEP separation region, the first passage and the second passage each have a different cross-sectional width perpendicular to the common path and perpendicular to a normal of the substantially planar assembly, and the first passage diverges from the second passage in a post-DEP separation region, the post-DEP separation region located downstream of the DEP separation region.

Embodiment 7: The 3-dimensional DEP sorting device of embodiment 6, further including: a third sub-layer of the electrically-insulating layer; a third passage located in the third sub-layer, wherein: the second sub-layer is interposed between the first sub-layer and the third sub-layer, the third sub-layer is interposed between the second sub-layer and the second electrode layer, the third passage follows the common path within the DEP separation region and is in direct fluid communication with the second passage within the DEP separation region, the third passage has a cross-sectional width perpendicular to the common path and perpendicular to the normal of the substantially planar assembly that is different from the cross-sectional width of the second passage, and the third passage diverges from the second passage in the post-DEP separation region.

Embodiment 8: The 3-dimensional DEP sorting device of embodiment 7, wherein the cross-sectional width of the second passage is less than the cross-sectional widths of the first passage and the third passage.

Embodiment 9: The 3-dimensional DEP sorting device of embodiment 7, wherein the cross-sectional width of the second passage is greater than the cross-sectional widths of the first passage and the third passage.

Embodiment 10: The 3-dimensional DEP sorting device of any one of embodiments 7 through 9, wherein the first passage, the second passage, and the third passage are substantially centered over one another in a direction perpendicular to the common path and parallel to the substantially planar assembly.

Embodiment 11: The 3-dimensional DEP sorting device of embodiment 6, further including one or more additional passages, each located in an additional sub-layer, wherein: the one or more additional passages includes a third passage, the one or more additional passages follow the common path within the DEP separation region of the electrically-insulating layer and are in direct fluid communication with one another and the first passage and the second passage within the DEP separation region, the one or more additional passages each have a cross-sectional width perpendicular to the common path and perpendicular to the normal of the substantially planar assembly, the cross-sectional width of each particular additional passage is different from the cross-sectional width of each additional passage neighboring that particular additional passage, and at least one of the one or more additional passages diverges from the second passage in the post-DEP separation region.

Embodiment 12: The 3-dimensional DEP sorting device of any one of embodiments 6 through 11, wherein the first electrode layer and the second electrode layer include patterned electrodes in the DEP separation region.

Embodiment 13: The 3-dimensional DEP sorting device of any one of embodiments 6 through 11, wherein the first electrode layer and the second electrode layer are substantially flat plates with electrically-conductive surfaces facing the electrically-insulating layer.

Embodiment 14: The 3-dimensional DEP sorting device of embodiment 13, wherein the electrically-conductive surfaces extend across substantially all of the electrically-insulating layer.

Embodiment 15: The 3-dimensional DEP sorting device of embodiment 13, wherein the electrically-conductive surfaces are substantially uniform in a region bounded by the DEP-separation region and sidewalls of the first passage or a region bounded by the DEP-separation region and sidewalls of the second passage.

Embodiment 16: The 3-dimensional DEP sorting device of any one of embodiments 13 through 15, wherein one or both of the electrically-conductive surfaces is coated with an electrically non-conductive coating less than 2 µm in thickness.

Embodiment 17: The 3-dimensional DEP sorting device of any one of embodiments 6 through 16, wherein the electrically-insulating layer is a polydimethylsiloxane (PDMS) structure.

Embodiment 18: The 3-dimensional DEP sorting device of any one of embodiments 6 through 17, wherein the electrically-insulating layer is a polydimethylsiloxane (PDMS) structure formed by bonding multiple individual PDMS layers together.

Embodiment 19: The 3-dimensional DEP sorting device of embodiment 18, wherein: the first sub-layer is formed by one or more of the individual PDMS layers, and the second sub-layer is formed by one or more of the individual PDMS layers.

Embodiment 20: The 3-dimensional DEP sorting device of embodiment 18, wherein the electrically-insulating layer is a composite structure that includes a combination of different materials.

Embodiment 21: The 3-dimensional DEP sorting device of embodiment 20, wherein the electrically-insulating layer is a composite structure that includes non-PDMS materials suspended in PDMS.

Embodiment 22: The 3-dimensional DEP sorting device of any one of embodiments 6 through 21, wherein the first sub-layer has a thickness of approximately 1 µm to 100 µm and the second sub-layer has a thickness of approximately 10 µm to 100 µm.

Embodiment 23: The 3-dimensional DEP sorting device of any one of embodiments 6 through 22, wherein the first sub-layer has a thickness of approximately 100 µm to 500 µm and the second sub-layer has a thickness of approximately 100 µm to 500 µm.

Embodiment 24: The 3-dimensional DEP sorting device of any one of embodiments 6 through 22, wherein the first passage has a cross-sectional width of at least 1 µm and the second passage and the second passage has a cross-sectional width of at least 2 µm.

Embodiment 25: The 3-dimensional DEP sorting device of any one of embodiments 6 through 22, wherein the first passage has a cross-sectional width of less than 1 µm and the second passage has a cross-sectional width of less than 2 µm.

Embodiment 26: The 3-dimensional DEP sorting device of any one of embodiments 7 through 24, wherein the first passage and the third passage have different cross-sectional widths.

Embodiment 27: The 3-dimensional DEP sorting device of any one of embodiments 7 through 26, wherein the first passage, the second passage, and the third passage have an aggregate cross-section that is substantially in the shape of a sideways "H" within the DEP separation region, thereby causing particulates or cells with positive DEP that are entrained in a fluid to collect in the sorting passage when an alternating-current voltage is applied between the first electrode layer and the second electrode layer.

Embodiment 28: The 3-dimensional DEP sorting device of any one of embodiments 6 through 26, wherein the first passage, the second passage, and the third passage have an aggregate cross-section that is substantially in the shape of a "+" within the DEP separation region, thereby causing particulates or cells with negative DEP that are entrained in a fluid to collect in the sorting passage when an alternating-current voltage is applied between the first electrode layer and the second electrode layer.

Embodiment 29: The 3-dimensional DEP sorting device of any one of embodiments 6 through 27, wherein application of an alternating-current (AC) voltage across the first electrode layer and the second electrode layer causes a non-uniform electromagnetic field to develop within a fluid flowed through the first passage and the second passage within the DEP separation region, wherein the non-uniform electromagnetic field has an intensity that is biased towards one of the first passage or the second passage.

Embodiment 30: The 3-dimensional DEP sorting device of any one of embodiments 6 through 29, wherein the 3-dimensional DEP sorting device is incorporated into a hand-held device.

Embodiment 31: The 3-dimensional DEP sorting device of any one of embodiments 6 through 30, wherein the 3-dimensional DEP sorting device is coupled to a hand-actuated pumping device configured to drive a fluid sample through the first passage and the second passage of the sorting device.

Embodiment 32: A method of fabricating multi-layer polydimethylsiloxane (PDMS) microfluidic structures, the method including: a) depositing a first uncured PDMS gel onto a positive mold; b) compressing the first uncured PDMS gel between the positive mold and a stamping having a plate with a modulus substantially larger than that of PDMS and a thin layer of PDMS on a side of the plate facing the positive mold; c) curing the first uncured PDMS gel into a PDMS layer; d) releasing the PDMS layer from the positive mold, the PDMS layer having a mold interface surface that was engaged with the positive mold prior to release; e) transferring the PDMS layer to a receiving surface; f) bonding portions of the mold interface surface of the PDMS layer to the receiving surface; and g) releasing the PDMS layer from the PDMS stamping.

Embodiment 33: The method of embodiment 32, further including: repeating steps a) through g) for additional PDMS layers.

Embodiment 34: The method of any one of embodiments 32 through 33, wherein the thin layer of PDMS is less than 500 μm thick.

Embodiment 35: The method of any one of embodiments 32 through 34, wherein the thin layer of PDMS is between 10 and 30 microns thick.

Embodiment 36: The method of any one of embodiments 32 through 35, further including: spin coating the plate with a second uncured PDMS gel to form the thin layer of PDMS; and curing the second uncured PDMS gel.

Embodiment 37: The method of embodiment 36, wherein the second uncured PDMS gel has platinum-divinyltetramethyldisiloxane (C8H18OPtSi2) added to it.

Embodiment 38: The method of embodiment 36 or 37, wherein the second uncured PDMS gel has platinum-divinyltetramethyldisiloxane (C8H18OPtSi2) added to it in addition to a standard curing agent for the PDMS gel.

Embodiment 39: The method of embodiment 37, wherein the platinum-divinyltetramethyldisiloxane is part of a standard PDMS curing agent.

Embodiment 40: The method of any one of embodiments 37 through 39, wherein the platinum-divinyltetramethyldisiloxane is added in a quantity of between 16 to 20 μL per 10 g of PDMS base and 1 g of standard PDMS curing agent.

Embodiment 41: The method of any one of embodiments 37 through 40, wherein the thin layer of PDMS is treated with a CYTOP surface treatment.

Embodiment 42: A method of forming a hybrid polydimethylsiloxane (PDMS) stamping, the method including: preparing a PDMS base by adding a platinum catalyst and a curing agent to the PDMS base, wherein the PDMS base has a cured PDMS stiffness when cured; spin coating a plate having a substantially higher stiffness than the cured PDMS stiffness with the PDMS base; and curing the PDMS base, curing agent, and platinum catalyst into a soft PDMS layer.

Embodiment 43: The method of embodiment 42, wherein the platinum catalyst is platinum-divinyltetramethyldisiloxane (C8H18OPtSi2).

Embodiment 44: The method of embodiment 43, wherein platinum-divinyltetramethyldisiloxane is part of the curing agent.

Embodiment 45: The method of embodiment 43, wherein the platinum-divinyltetramethyldisiloxane is added from a separate source than the curing agent.

Embodiment 46: The method of any one of embodiments 43 through 45, wherein the platinum-divinyltetramethyldisiloxane is added in a quantity of between 16 to 20 μL per 10 g of PDMS base and 1 g of PDMS curing agent.

Embodiment 47: The method of any one of embodiments 42 through 46, wherein the thin layer of PDMS is treated with a CYTOP surface treatment.

These and other aspects of various embodiments are explained in more detail below. As will be apparent from the following explanation, these embodiments are illustrative and not limiting. In view of the teachings provided herein, numerous variation and modifications will be available to one of skill in the art.

BRIEF DESCRIPTION OF THE DRAWINGS

FIG. 1 depicts one example of a two-dimensional DEP cell sorter.

FIG. 2 depicts another example of a two-dimensional DEP cell sorter.

DETAILED DESCRIPTION

Figure 3A:
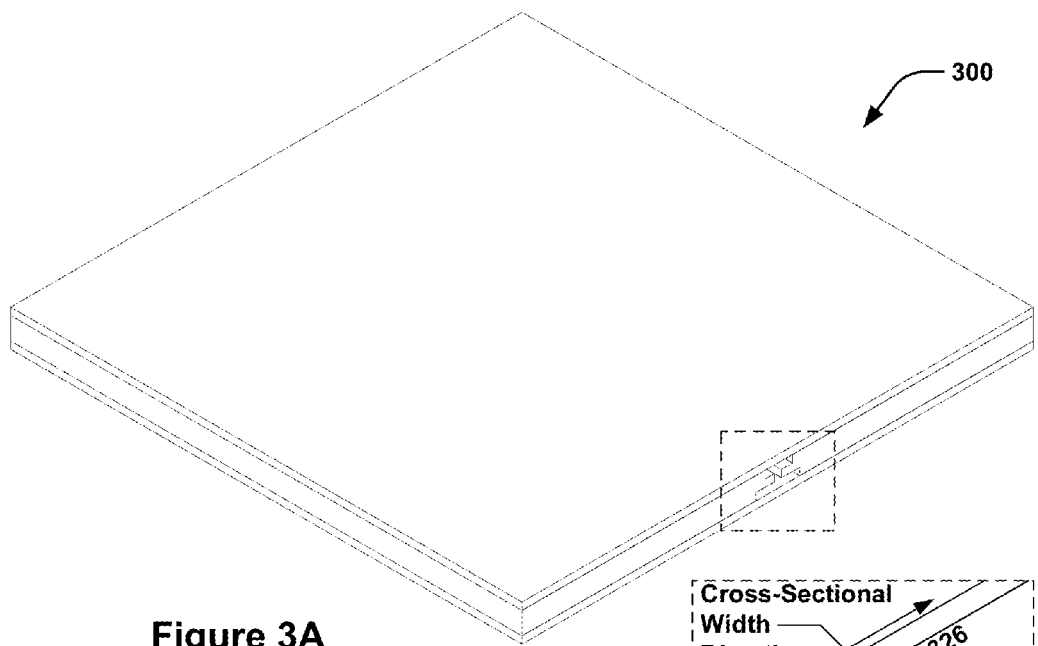
FIG. 3A depicts an isometric view of a portion of a three-dimensional DEP cell sorter FIG. 3A' is a detail view of the visible cross section of various passages of the cell sorter of FIG. 3A.
Figure 3A:
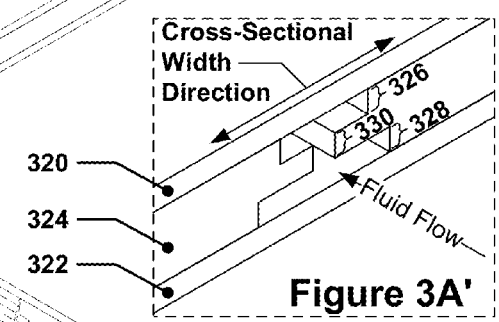

Examples of various implementations are illustrated in the accompanying drawings and described further below. It will be understood that the discussion herein is not intended to limit the claims to the specific implementations described. On the contrary, it is intended to cover alternatives, modifications, and equivalents as may be included within the spirit and scope of the invention as defined by the appended claims. In the following description, numerous implementation-specific details are set forth in order to provide a thorough understanding of the present invention. The present invention may be practiced without some or all of these implementation-specific details. In other instances, well-known process operations have not been described in detail in order not to unnecessarily obscure the present invention.

It is to be understood that while the discussion below may focus primarily on structures or devices such as cell sorters for sorting biological materials, e.g., cells, microorganisms, etc., such structures may be used to sort any particulates or objects that may be responsive to DEP sorting techniques. Accordingly, the concepts and structures discussed herein are not limited solely to cell sorting applications, but may be applied to various other sorting applications as well, e.g., sorting of DNA, particulates, molecules, etc.

It will also be understood that, in various locations within this disclosure and in the Figures, that particulates or cells may be represented by simple geometric shapes, e.g., circles, squares, and stars. Such a convention was adopted for clarity and is to be interpreted as merely indicating different kinds of cells or particulates as opposed to particulates or cells actually having those shapes.

It is to be further understood that the structures and techniques discussed herein are provided in the context of microfluidic structures, e.g., structures that geometrically constrain fluids to volumes that are sub-millimeter scale in at least one dimension. Microfluidic structures are typically provided in the form of a microfluidic chip, which may be a hard material, soft material, or combination of hard and soft materials that have one or more fluid passages or channels provided within through which fluids may flow. The one or more passages may transport fluid between various areas of the microfluidic chip, including chambers, inlet ports, outlet ports, reactors, valves, pumps, sorting devices, etc. The overall working volume of fluid within a given microfluidic chip may, of course, vary with the density, as well as dimensions, of microfluidic features within the chip as well as the overall size of the microfluidic chip. Such fluid working volumes may typically be in the sub-µL range for a 10 cm square microfluidic chip. Typical passage and channel widths and/or depths may often be on the order of between hundreds of micrometers to nanometers. In some instances, such widths and/or depths may be on the sub-mm scale. Typical passage and channel lengths, however, may be on the order of micrometers to millimeters in length. Due to the small size of microfluidic structural features, traditional machining processes may often prove to be unsuited to producing such structures. As a result, microfluidic structure fabrication may, in many cases, rely on at least some concepts drawn from semiconductor fabrication, e.g., photolithography techniques similar to those used to produce micro- and nano-scale features for semiconductor microchips may be used to manufacture features in the microfluidics context.

Figure 3B:
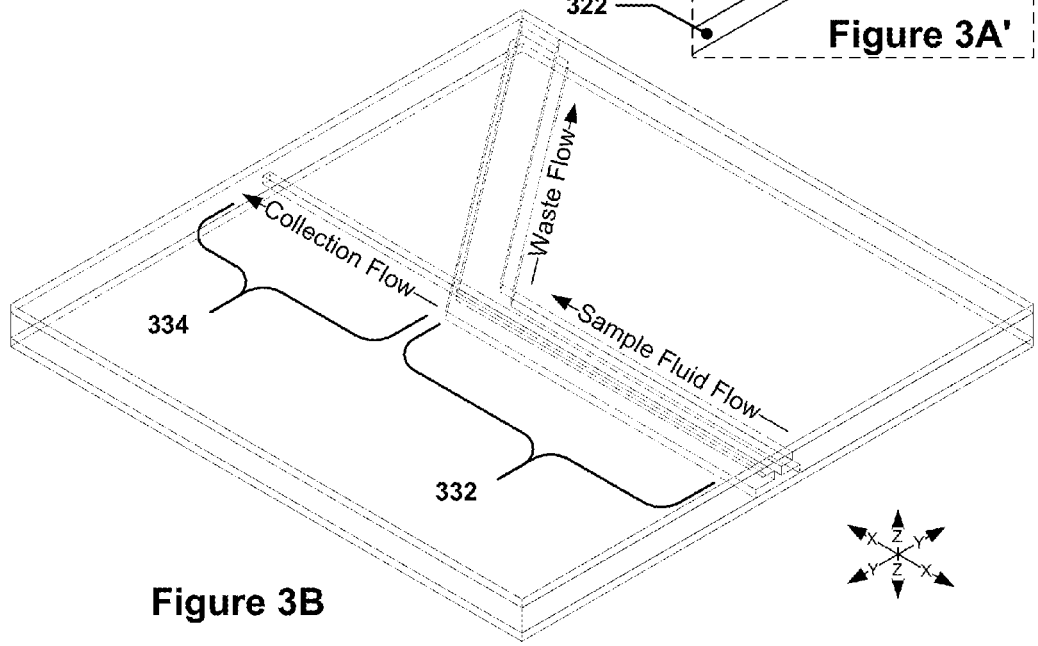
FIG. 3B is a hidden-line version of FIG. 3A that shows internal features not visible in FIG. 3A.
Figure 3C:
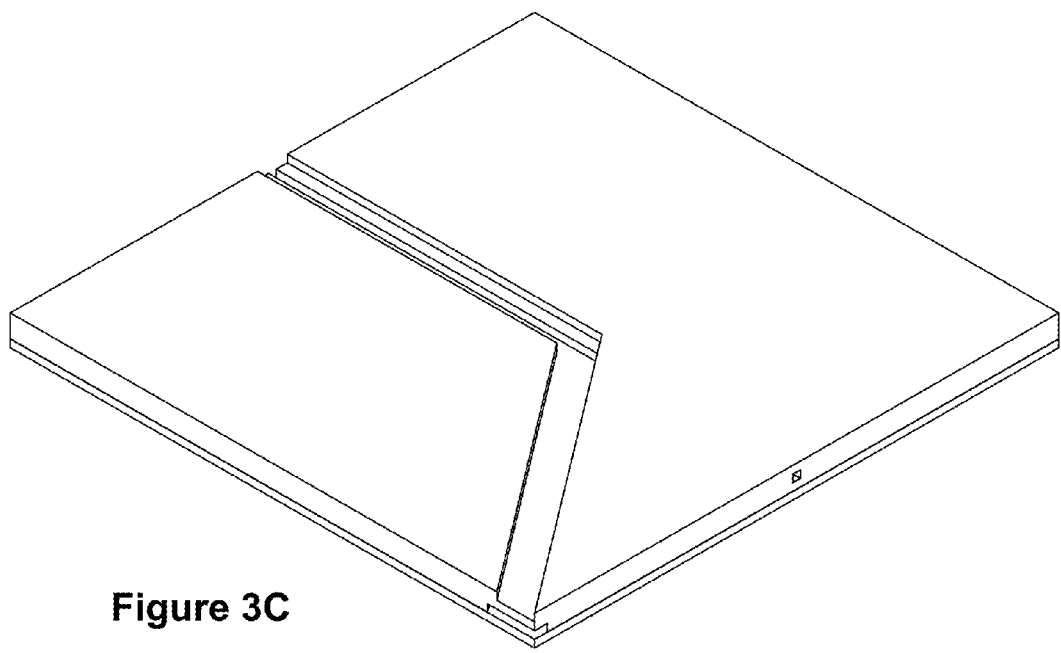
FIGS. 3C and 3D depict reverse isometric views of the cell sorter of FIG. 3A.
Figure 3D:
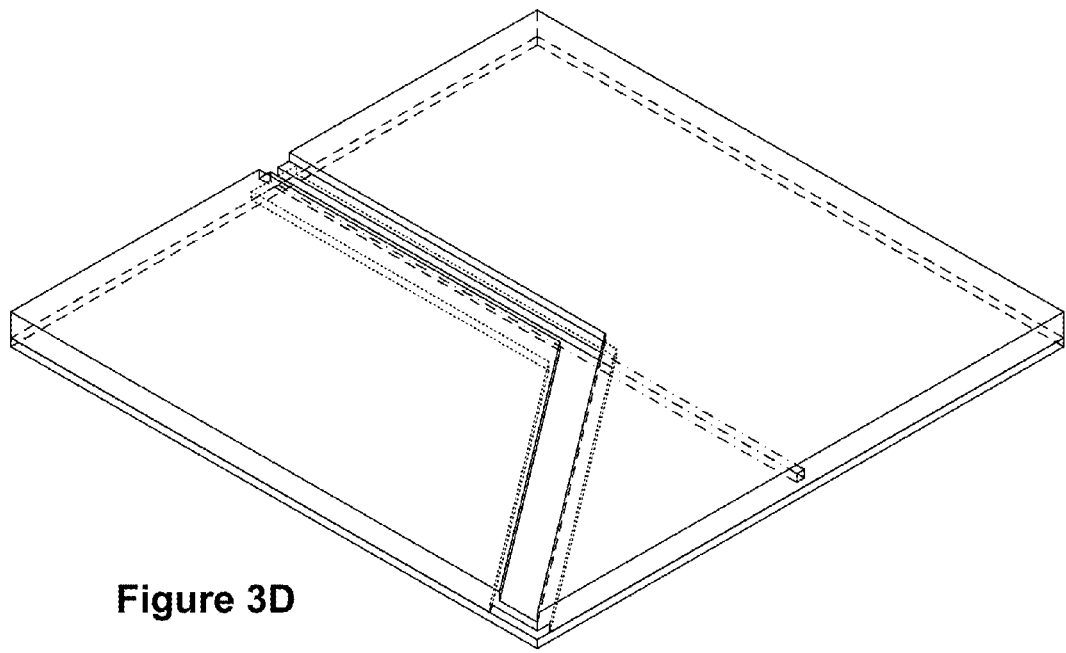

FIG. 3A depicts an isometric view of a portion of a three-dimensional DEP cell sorter 300 similar to the cell sorter shown in FIGS. 1A, 1B, and 1C of U.S. Provisional Patent Application 61/616,385 and in FIGS. 3a, 3b, and 3c on page 39 of U.S. Provisional Patent Application 61/799,451. FIG. 3A' is a detail view of the visible cross section of various passages of the cell sorter 300. FIG. 3B is a hidden-line version of FIG. 3A that shows internal features not visible in FIG. 3A. FIGS. 3C and 3D depict reverse isometric views of the cell sorter 300.

An electrically-insulating layer 324 may be sandwiched between a first electrode layer 320 and a second electrode layer 322. The first electrode layer 320 and the second electrode layer 322 may, for example, be provided by glass or plastic substrates with an indium-tin-oxide (ITO) conductive coating on the surfaces facing the electrically-insulating layer 324. Other substrates and electrically conductive coatings (or materials that are naturally electrically conductive without requiring a coating) may be used to provide the first electrode layer 320 and the second electrode layer in some implementations.

The electrically-insulating layer 324 may include a first passage 326, a third passage 328, and a second passage 330. The second passage 330 may be located between the first passage 326 and the third passage 328 within a DEP separation region 332 of the cell sorter 300. The first passage 326 may be located between the first electrode layer 320 and the second passage 330, and the third passage 328 may be located between the second electrode layer 322 and the second passage 330. The second passage 330, the first passage 326, and the third passage 328 may all be contiguous with one another within the DEP separation region 332, e.g., fluid flow between the three passages in a direction normal to the nominal layer plane of the cell sorter 300 may be unimpeded by physical barriers. The electrically-insulating layer may be made of PDMS or other material with high electrical resistivity.

Downstream of the DEP separation region 332, the second passage 330 may diverge from the paths followed by the first passage 326 and the third passage 328. While the first passage 326 and the third passage 328 are shown following common paths downstream of the DEP separation region 332, in some implementations, the first passage 326 and the third passage 328 may follow different or even opposing paths downstream of the DEP separation region 332.

As can be seen, the second passage 330, the first passage 326, and the third passage 328 each have a cross-sectional width in the DEP separation region 332 that is perpendicular to the nominal fluid flow direction and substantially perpendicular to the nominal layer plane of the cell sorter 300. The cross-sectional width of the second passage 330 may be less than the cross-sectional widths of the first passage 326 and the third passage 328. When an AC voltage is applied across the first electrode layer 320 and the second electrode layer 322, an electromagnetic field is created within the fluid sample that is flowing through the first passage 326, the third passage 328, and the second passage 330 within the DEP separation region 332. Due to the smaller cross-sectional width of the second passage, the electromagnetic field may be concentrated in or biased towards the second passage 330. This may cause particles attracted to the field due to DEP, i.e., particles with positive DEP, to migrate into the second passage 330, and particles repulsed by the field due to DEP, i.e., particles with negative DEP, to migrate into or towards the first passage 326 or the third passage 328.

Figure 4A:
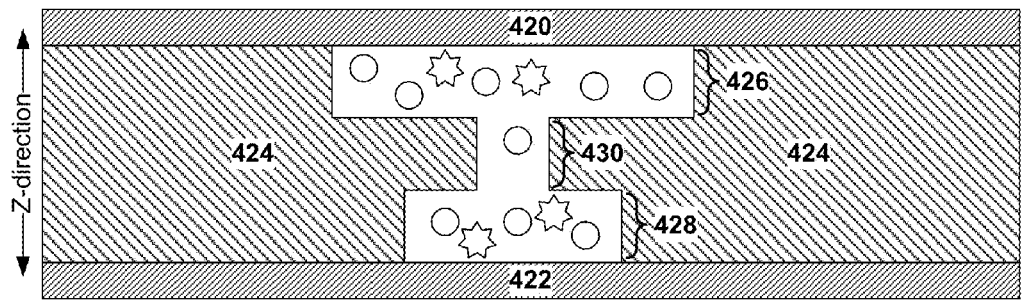
FIGS. 4A through 4C depict cross-sections of an example of a three-dimensional cell sorter in a DEP separation region.
Figure 4B:
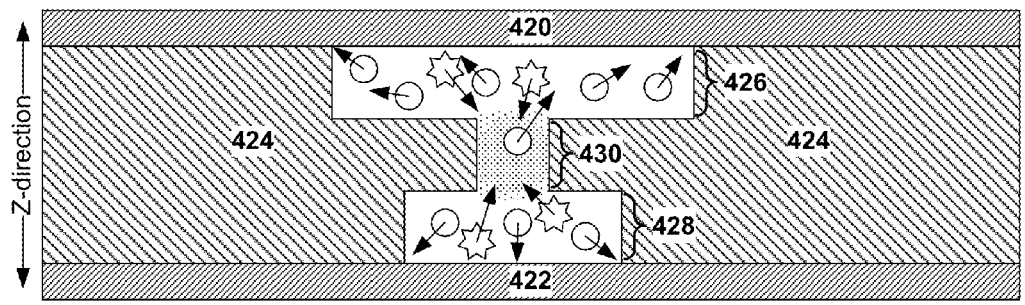
Figure 4C:
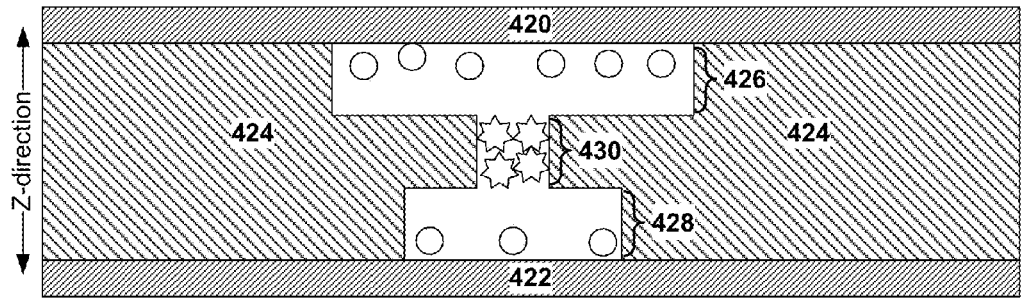
Figure 4D:
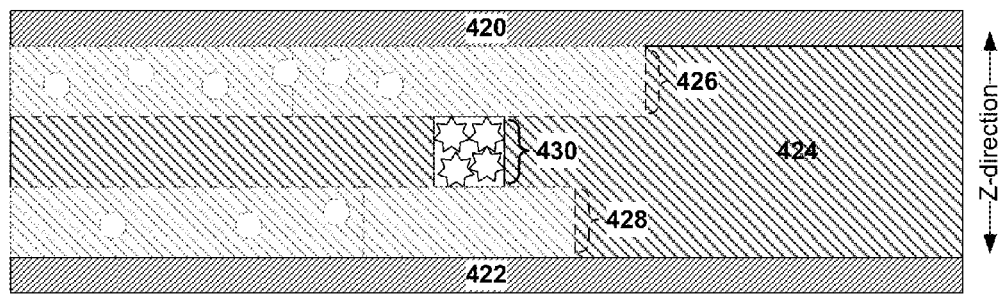
FIG. 4D depicts a cross-section of the three-dimensional cell sorter of FIGS. 4A through 4C in a post-DEP separation region.

FIGS. 4A through 4C depict cross-sections of an example of a three-dimensional cell sorter in the DEP separation region; FIG. 4D depicts a cross-section of the three-dimensional cell sorter of FIGS. 4A through 4C in the post-DEP separation region.

In FIG. 4A, a fluid sample with a mixture of round cells and star cells is entrained in the first passage 426, the third passage 428, and the second passage 430; the fluid flow direction is normal to the page. As can be seen, the widths of the first passage 426 and the third passage 428 are both wider than the width of the second passage 430. While each passage is shown as having substantially the same thickness, e.g., ⅓ of the total thickness of electrically-insulating layer 424, the passages may also have differing thicknesses. The passages may form a continuous fluid flow region between a first electrode layer 420 and a second electrode layer 422.

In FIG. 4B, an AC voltage has been applied across the first electrode layer 420 and the second electrode layer 422, producing an electromagnetic field (shaded area) concentrated near the second passage 430. In this implementation, the frequency of the electromagnetic field is such that star cells are attracted to the field by DEP, and round cells are repelled from the field by DEP. Arrows are provided to indicate the general migration direction of the cells. It is to be understood that the electromagnetic field may be present in FIG. 4A and 4C as well, although it is not shown—due to the structure of the cell sorter shown in FIGS. 4A through 4D, the fluid sample may be subject to DEP throughout substantially the entire DEP sorting region.

It is to be understood that while the electrode layers shown in FIGS. 4A through 4C are shown as being in direct contact with the fluid in the first and third passages 426 and 428, the electrode layers 420 and 422 may also have a thin, electrically-insulating, i.e., non-conducting, coating that separates the electrode layers 420 and 422 from the fluid sample. If the coating is thin enough, e.g., on the order of approximately 2 μm or less, the AC voltage frequency used may be high enough that the thin layer does not block electromagnetic field penetration into the liquid sample in a manner that substantially impacts the electromagnetic field pattern within the liquid sample. This may allow the electrode layers 420 and 422 to be coated with electrically-insulating materials that may prevent (or, if desired, encourage) cell or particle adhesion to the electrode layers.

In FIG. 4C, the fluid sample has been exposed to the electromagnetic field for a sufficiently long enough period of time that DEP-induced migration of the star cells to the second passage 430 has occurred, and DEP-induced migration of the round cells to the first passage 426 and the third passage 428 has occurred.

In FIG. 4D, the fluid sample is split into two streams by diverting the first passage 426 and the third passage 428 from the second passage 430. The first passage 426 and the third passage 428 are shown using hidden lines since they branch away from the second passage 430 within the electrically-insulating layer 424. This causes the star cells concentrated in the second passage to be physically separated from the round cells in the first passage 426 and the third passage 428.

Figure 4E:
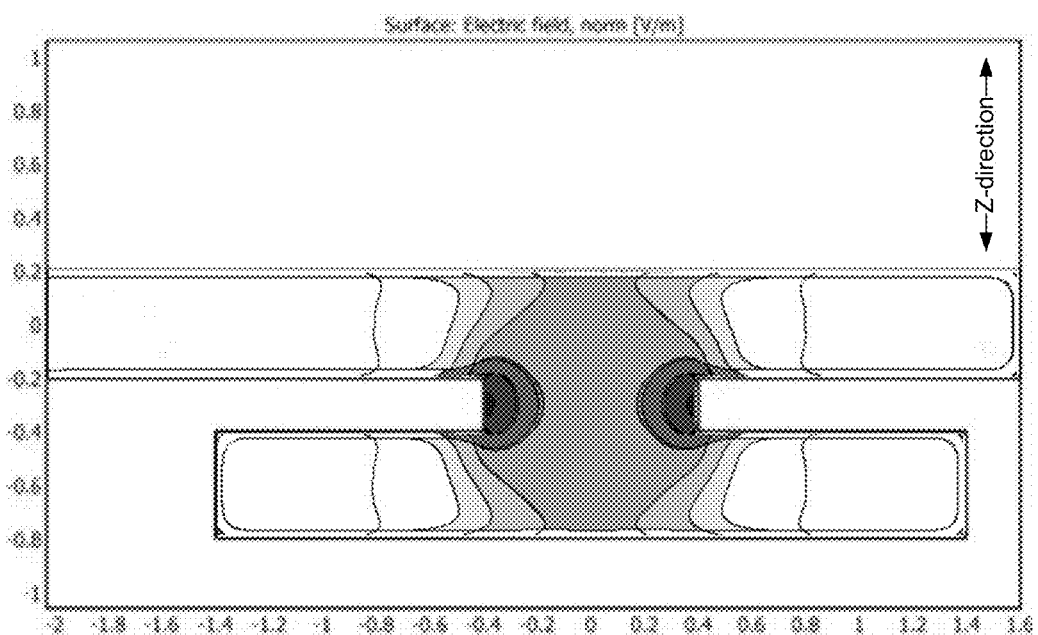
FIG. 4E depicts a cross-sectional view a simulation of electromagnetic field strength in a three-dimensional DEP cell sorter.

FIG. 4E depicts an analysis plot showing the electromagnetic field strength through a cross-section of a three-dimensional DEP cell sorter. In FIG. 4E, darker shading indicates increasing electromagnetic field strength, whereas lighter shading indicates the opposite. As can be seen, electromagnetic field strength is biased towards the center elevation in the z-direction of the three-dimensional DEP cell sorter.

In two-dimensional cell sorters, the electromagnetic field intensity is governed by the shape of the electrodes—in order to generate the desired electromagnetic field shape, the electrodes must be suitably patterned. By contrast, the electromagnetic field intensity in a three-dimensional DEP cell sorter such as that depicted in FIGS. 3A through 3D is governed by the relative widths of the first passage, the third passage, and the second passage. This allows the electromagnetic field intensity, and thus the DEP effect on the entrained cells, to be decoupled from the shape of the electrodes, allowing the electrode layers to simply be flat, non-patterned electrodes. Of course, a patterned electrode may still be used if desired, although this may change the electromagnetic field strength, and thus the performance of the cell sorter, in some cases. In some implementations, an array of cell sorters may be provided in a common electrically-insulating layer, each with an individual planar electrode that may be electrically isolated from the planar electrodes of the other cell sorters, yet still located on a common substrate—in such cases, of course, some layer-level electrode patterning may exist to allow voltages to each cell sorter to be applied in isolation, but the electrodes at the individual cell sorter level may be "unpatterned." In many implementations, the electrodes may extend along the entire length of the passages within the DEP-separation region. In other implementations, however, the electrodes may stop prior to the divergence of the second passage from the first passage and the third passage—in such implementations, however, the concentrated cells may begin to migrate out of the second passage due to the absence of the electromagnetic field in the electrode-less region of the DEP-separation region, thus reducing cell sorting performance. While a three-dimensional DEP cell sorter may be implemented with a uniform electrode in the DEP separation region, some implementations of such a cell sorter may utilize patterned electrodes in the DEP separation region.

Because the electrodes may remain relatively uniform along the entire length of the second passage 330 within the DEP separation region 332, the electromagnetic field generated within the sample fluid may also be relatively constant along this same length. This causes the DEP forces generated by such a field to act continuously on cells flowing down the first passage 326, the third passage 328, and the second passage 330 throughout the entire DEP separation region 332, regardless of the flow rate of the fluid sample. In effect, the only major restrictions on fluid flow rate with respect to sorting effectiveness is that the flow rate must be low enough that cells in the first channel 326 and the second channel 328 are exposed to DEP forces for a long enough time period to allow them to move from the first channel 326 and the second channel 328 and into the sorting channel 330, and that the flow rate be low enough that the shear stress experienced by cells in the flow be survivable, e.g., on the order of 10 m/sec.

Because the DEP cell sorter discussed above is largely insensitive to sample flow rate, active control of sample flow rate is not necessary as it is with existing two-dimensional DEP cell sorters. In fact, a three-dimensional DEP cell sorter may even be manually driven, e.g., using a hand-activated squeeze bulb or bellows to drive fluid flow through the sorter. This may eliminate the need for a bulky pump with precise pressure control in many microfluidic systems. Using three-dimensional DEP cell sorters in a large-scale array may allow, for example, a 2 cm wide chip that could support 100 separate 100 micron-wide sorters, be hand-powered, and achieve 10 ml/min of throughput.

While the above discussion has focused on a three-dimensional DEP cell sorter that focuses positive DEP cells into the second passage, other passage configurations may be used as well. For example, if the second passage has a larger width than the first passage and the third passage, e.g., forming a "+" cross-section, then the resulting electromagnetic field that is generated may be concentrated in the first and third passages rather than the second passage. This may cause cells with negative DEP to congregate in the second passage and cells with positive DEP to congregate in the first passage and the third passage. A three-dimensional DEP cell sorter with such a cross-section may be used to collect negative DEP cells.

Generally speaking, three-dimensional DEP cell sorters function by sorting cells primarily in the "z" direction, i.e., normal to the overall plane of the electrode layers and the electrically-insulating layer. This may be accomplished by customizing the electromagnetic field that drives DEP movement of cells to vary as a function of z-direction position with respect to the electrode layers. Such electromagnetic field customization may be accomplished by varying the cross-section of the passages through which sample fluid flows and within which the electromagnetic field is generated. By varying the cross-sectional geometry of these passages in the z-direction, some zones of the passage along the z-axis having an electromagnetic field concentration may attract target cells having positive DEP, whereas other zones of the passage along the z-axis having a dilute electromagnetic field may attract target cells having negative DEP. In three-dimensional cell sorters, migration of cells in a direction transverse to the fluid flow direction is decoupled from the fluid flow rate and is instead driven by forces produced by DEP effects. Thus, in both zero-flow and high-flow situations, the DEP effect is capable of migrating the cells in the z-direction and into the collection region.

By contrast, two-dimensional DEP cell sorters function by sorting cells in the "y" direction, i.e., transverse to the fluid flow direction (the "x" direction) and parallel to the overall plane of the electrode layers and the electrically-insulating layer. In such two-dimensional DEP cell sorters, the electromagnetic field is customized by patterning the electrodes on the electrode layers so that the electromagnetic fields produced have a pattern in the x-y plane that is at an angle to the fluid-flow direction. The combination of forces provided by the fluid flow and the DEP effect in a two-dimensional DEP cell sorter cause the cells to migrate in the y-direction—if the cells migrate in the y-direction far enough, then they may be shunted into a collection channel. This transverse movement, however, is directly linked to the fluid flow speed—if there is no fluid flow, then the cells will not migrate (aside from some small movement towards the electrodes). If there is too much fluid flow, the fluid flow forces will overcome the DEP forces and the cell may be pushed out of the DEP effect area and not migrate far enough to be in the collection channel by the time the fluid sample reaches the waste and collection channels.

In practice, three-dimensional cell sorters may improve on two-dimensional cell sorters by two to three orders of magnitude or more with respect to throughput, putting them on par with other technologies, such as inertial cell sorters. In contrast to such other technologies, however, the three-dimensional cell sorter may be packaged in a much smaller volume.

It is to be understood that while the three-dimensional DEP cell sorters discussed above feature a set of three passages in a sideways-"H" configuration, other three-dimensional DEP cell sorters may feature other cross sections and numbers of passages. For example, a two-passage DEP cell sorter may be made where one of the passages is of a different width than the other passage. Greater numbers of passages are also possible. For example, 7 passages may be provided in a three-dimensional DEP cell sorter—each odd-numbered passage may be wider than the even-numbered passages, resulting in a concentrated electromagnetic field in each even-numbered passage. Cells or particulates may thus migrate from the odd-numbered passages into the even-numbered passages in the DEP-separation region when the electromagnetic field is present. Each even-numbered passage may diverge from the odd-numbered passages in the post-DEP separation region. In some such implementations, each even-numbered passage may be routed to a different location—in the example given, this may allow for three separate batches of cells to be extraction from a common sample while allowing for three different post-extraction analyses to be performed on the extracted cells.

In some implementations, the cross-sectional variation in the z-direction of the passages may be provided dynamically. For example, a fluid passage for sample fluid flow may be provided, e.g., a rectangular cross-section passage. The fluid passage may have a floor and a ceiling provided by electrode layers. Two parallel passages may be located next to the fluid passage, one on either side. The parallel passages may be separated from the fluid passage by a thin, deformable wall. If the parallel passages are pressurized, e.g., with a gas or a liquid, the pressure may cause the deformable walls to distend into the fluid passage, causing a narrowing in the cross section of the fluid passage commensurate with the degree of deflection in the thin walls. An electromagnetic field produced by applying a voltage across the electrode layers may concentrate at the narrowing point, and positive DEP particulates or cells may then gather at that location. Conversely, if a vacuum is drawn on the parallel passages, this may cause the deformable walls to distend into the parallel passages, causing the fluid passage to bulge outwards. This may cause cells with a negative DEP to concentrate near the point of maximum bulge deflection.

Figure 5A:
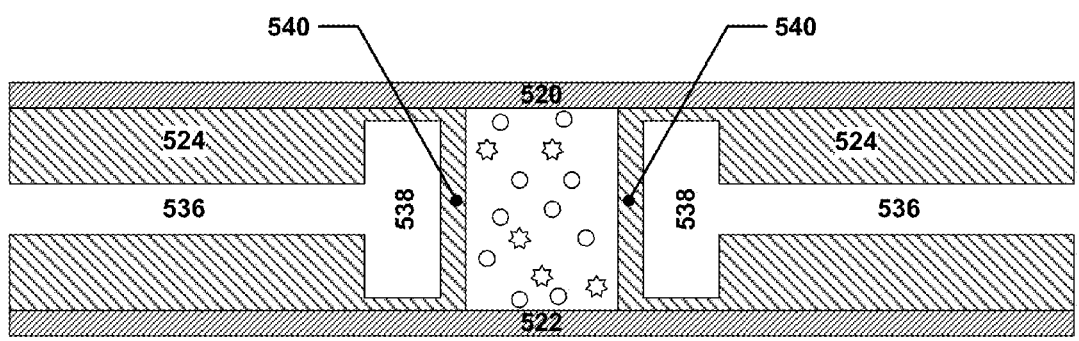
FIGS. 5A through 5C depict cross-sectional views of a microfluidic cell sorter structure having a dynamically-variable passage cross-section.
Figure 5B:
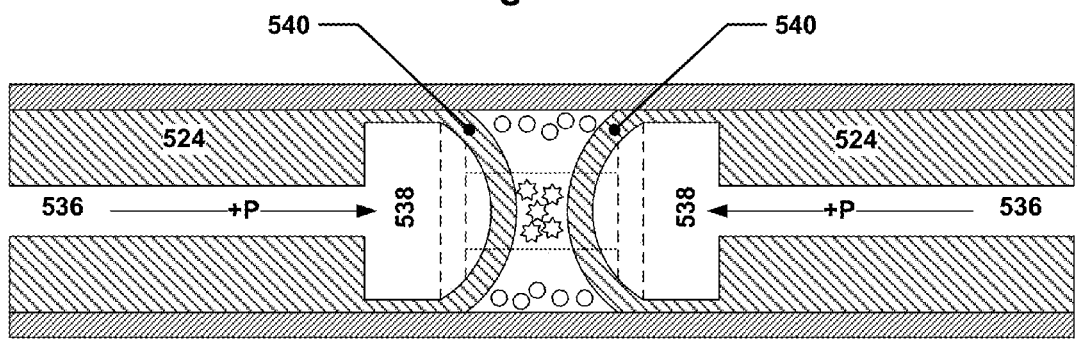
Figure 5C:
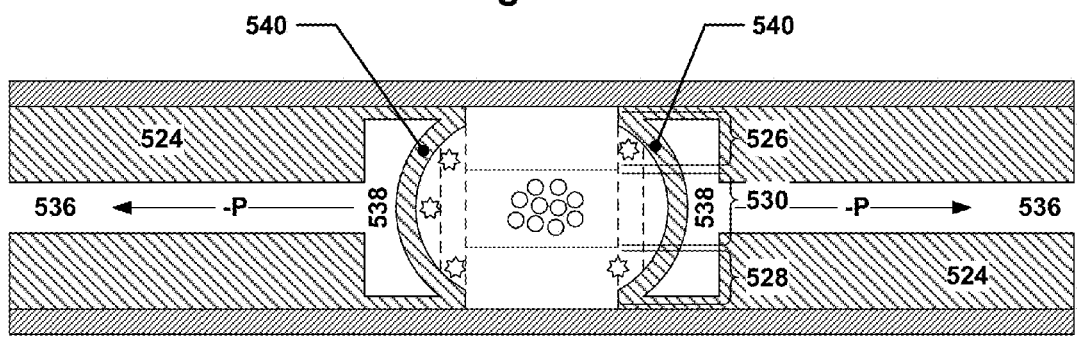

FIGS. 5A through 5C depict cross-sectional views of a microfluidic cell sorter structure having a dynamically-variable passage cross-section. As can be seen, an electrically-insulating layer 524 may be sandwiched between a first electrode layer 520 and a second electrode layer 522. A fluid flow passage 542 may be bounded by the first electrode layer 520 along an upper side and the second electrode layer 522 along a lower side; it is to be understood that the terms "upper" and "lower" are used to refer to the orientation of such boundaries with respect to the Figure, and may not be reflective of the actual orientation of such boundaries in an actual implementations.

The fluid flow passage 542 may also be bounded by thin walls 540, which may separate the fluid flow passage 542 from side passages 538 that may be configured to run substantially parallel to the fluid flow passage 542. The thin walls 540 may have a substantially uniform thickness with respect to the distance between the fluid flow passage 542 and the side passages 538. The side passages 538 may be configured to be fluidly isolated from the fluid flow passage 542. Actuation ports 536 may be provided and may be in fluid communication with the side passages 538. The actuation ports 536 may be used to provide a pressure differential between the fluid flow passage 542 and the side passages 538. Depending on the nature of the pressure differential, the thin walls 540 may distend into the fluid flow passage 542, as is shown in FIG. 5B for a greater pressure in the side passage 538, or into the side passages 538, as is shown in FIG. 5C for a lesser pressure in the side passage 538. Dashed lines show the location of the thin walls 540 prior to deflection.

When an AC voltage is applied between the first electrode layer 520 and the second electrode layer 522, a DEP effect may be generated within a fluid pumped through the fluid passage 542. In Figure A, the cross-section of the fluid passage 542 may be relatively constant, and there may be little to no concentration of cells, e.g., of round cells and star cells, in any one region of the fluid passage 542 due to the DEP effect. However, if the thin walls 540 are distended into the fluid passage 542 by a positive pressure differential between the side passages 538 and the fluid passage 542, then this may cause the electromagnetic field generated within the fluid to be concentrated on or biased towards the narrowest portion of the cross section of the fluid passage 542, e.g., the center of the fluid passage 542 in this example. In this case, the star cells are positive DEP cells at the frequency used for the AC voltage and are attracted to the center of the fluid passage 542 where the DEP effect is the most pronounced.

If the thin walls 540 are instead distended into the side passages 538, the electromagnetic field may be weakest at or biased away from the center of the fluid passage 542. This may cause negative DEP cells at the frequency used to migrate towards the center of the fluid passage 542.

This dynamic structure may allow for a single structure to be used to sort cells or particulates exhibiting both negative and positive DEP, depending on how the thin walls are deformed. Such a DEP sorting structure may be used in an implementation similar to that shown in FIGS. 3A through 3D in the DEP sorting region 332 to segregate desired cells from a larger sample.

It is to be understood that the thin walls may be deformed dynamically, e.g., transitioned from an un-deformed state to a deformed state or from one deformed state to another as needed, or may be deformed permanently as part of a manufacturing process. For example, it may be desirable in some instances to fabricate the electrically-insulating layer of a three-dimensional DEP cell sorter in a single layer fabrication process, as opposed to multiple layers requiring alignment with one another. In such cases, a structure similar to that shown in FIGS. 5A through 5C may be used, except that the side passages 538 and the actuation ports 536 may instead extend all the way to the first electrode layer 520 and the second electrode layer 522 in the z-direction. After the electrically-insulating layer has been sandwiched between the electrode layers, PDMS gel or other substance may be flowed into the side passages 538 to displace air or gas. The PDMS gel or other substance may then be pressurized to distend the thin walls 540 into the fluid passage 542 or partially suctioned out to distend the thin walls 540 into the side passages 538. Once the fluid passage 538 reaches the desired cross-section, the PDMS gel or other substance may be sealed off to prevent alteration of the thin wall distension, or may even be cured so as to solidify and form substantially rigid structure. Such techniques may also be practiced with other dynamically-variable structures that are not capable of being manufactured as a single-layer electrically-insulating layer.

Figure 6A:
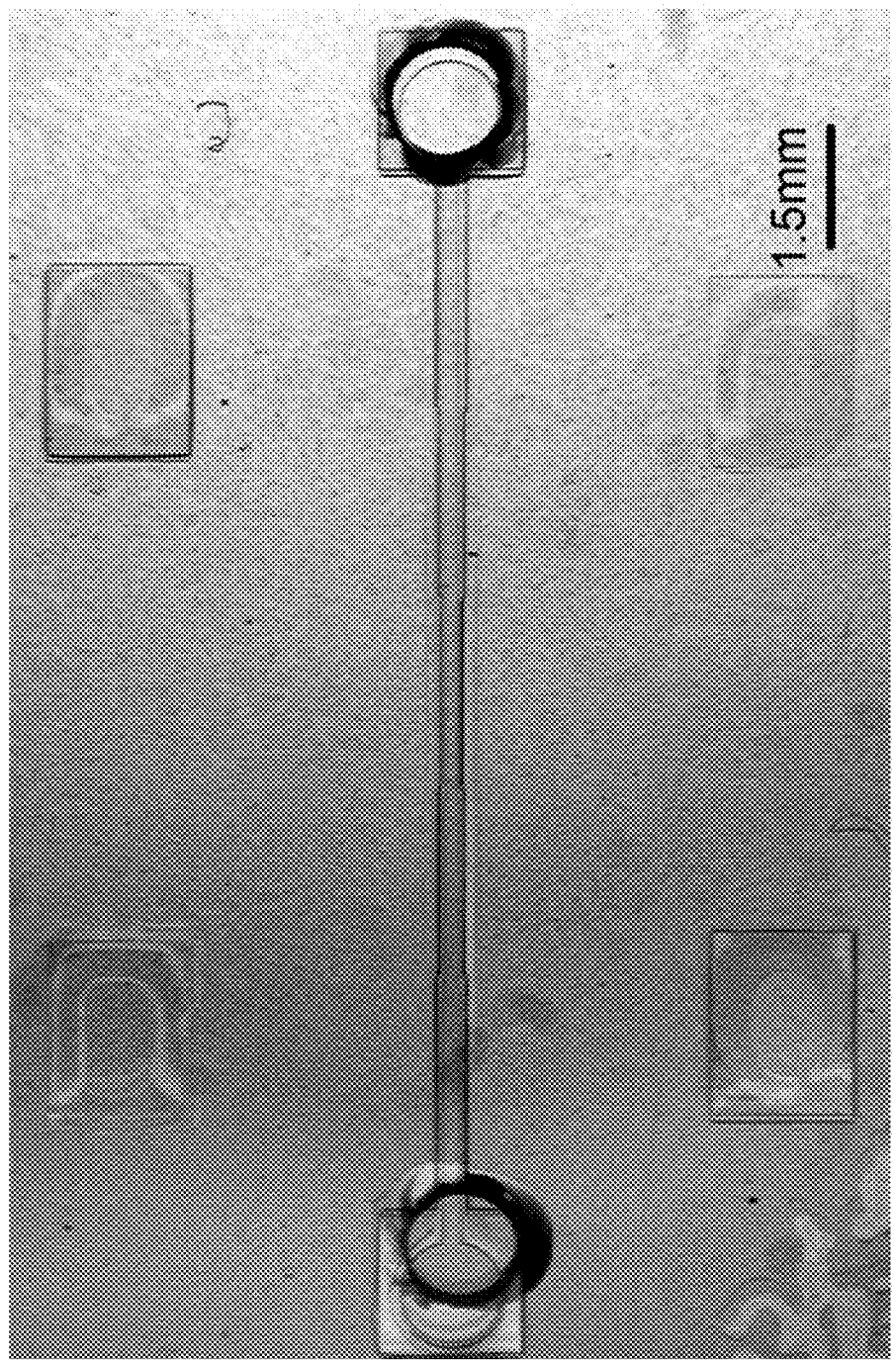
FIG. 6A depicts an image of a three-dimensional DEP cell sorting structure captured through a microscope.
Figure 6B:
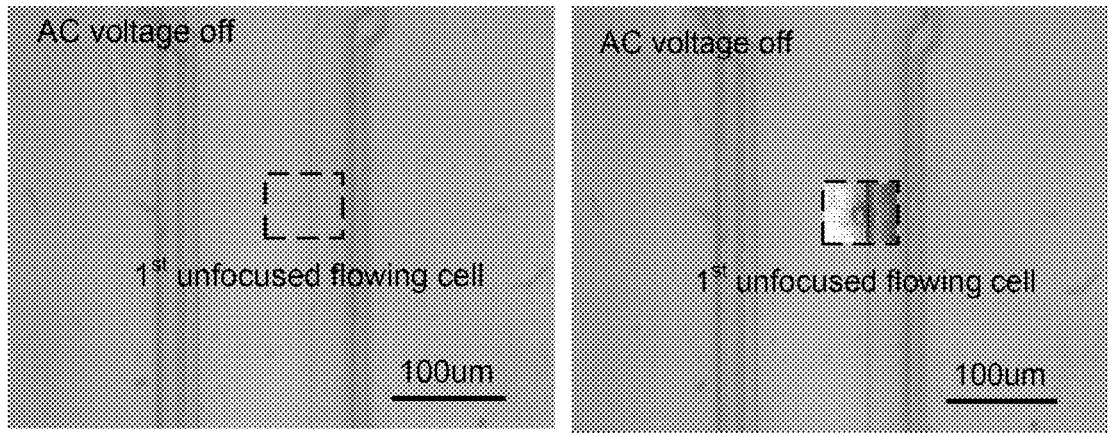
FIGS. 6B-6D depict further images captured through a microscope of a DEP sorting region of the three-dimensional DEP cell sorting structure of FIG. 6A.
Figure 6C:
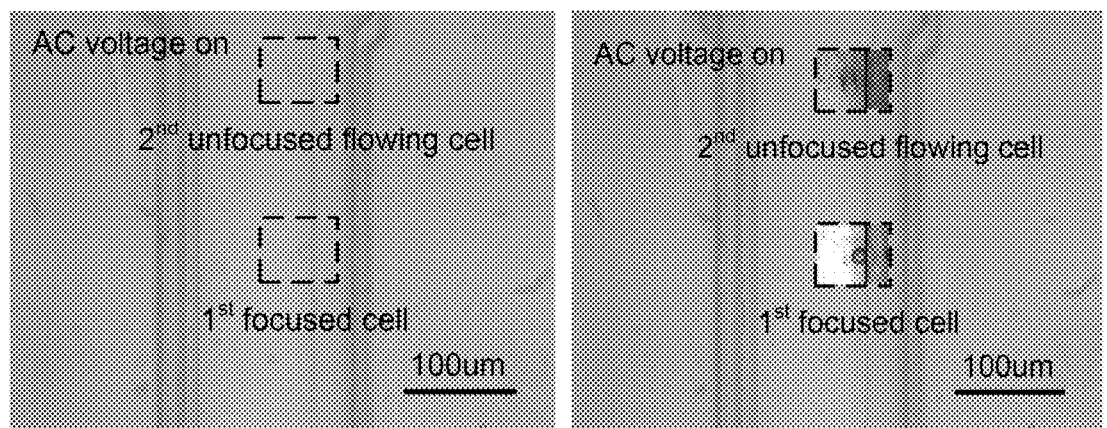
Figure 6D:
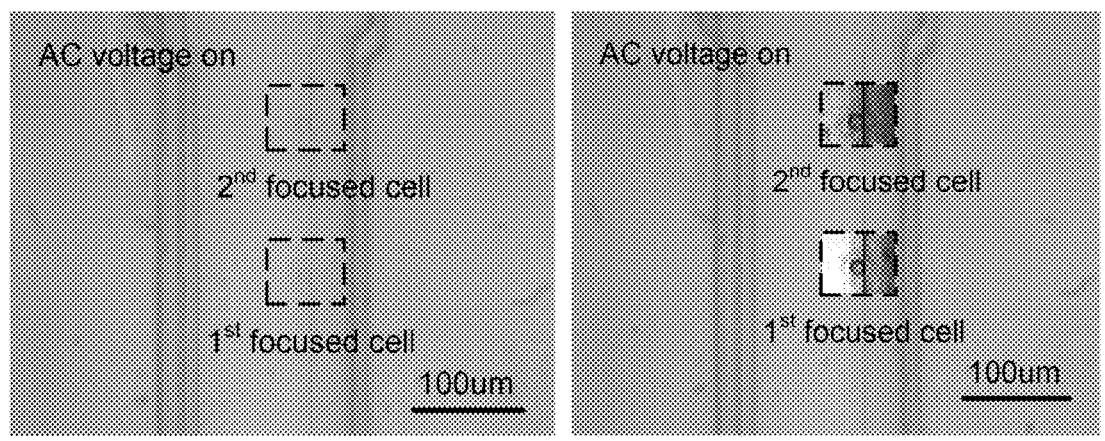

It is to be understood that, in some implementations, complete physical separation of desired cells from the fluid sample via a collection passage may not be desired, e.g., in some implementations, merely separating the desired cells from other cells in the fluid sample in the z-direction, i.e., in a direction orthogonal to the overall plane of the cell sorter microfluidic structure, may be sufficient. For example, FIGS. 6B-6D depict images captured through a microscope of a DEP sorting region of a prototype three-dimensional DEP cell sorting structure with a sample fluid flowing through it from the top of the page to bottom of the page; the three-dimensional cell sorting structure is shown in overview in FIG. 6A. For clarity, each image in FIGS. 6B through 6C is reproduced twice, with the original image on the left and a contrast-enhanced image on the right. The contrast-enhanced images have only been contrast-enhanced within the dashed rectangle or rectangles on each image.

FIG. 6A through 6D's perspectives are plan view, i.e., the viewing directions are normal to the overall plane of the microfluidic structure. The portion that is shown in FIGS. 6B through 6C may, for example, correspond to the DEP separation region 332 from FIGS. 3A through 3D. The microscope used to capture the images for FIGS. 6B through 6D is focused on a focal plane corresponding to a passage that, for example, corresponds to the second passage 330 of FIGS. 3A through 3D or the second passage 430 of FIGS. 4A through 4C. Cells that are in passages above or below the passage in the focal plane will be out of focus, whereas cells that are within the passage in the focal plane will be in-focus (or at least more in-focus).

In FIG. 6B, the AC voltage that provides the DEP effect has not been applied. A dashed rectangle outlines an area where an "unfocused" cell is barely visible and is not in sharp focus. This cell is slightly more visible in the contrast-enhanced region of the right-hand image.

In FIG. 6C, the AC voltage that provide the DEP effect has been applied to electrode layers on top of and beneath the three-dimensional DEP cell sorting structure. The electrode layers may, for example, be ITO-coated glass so as to be substantially optically transparent to facilitate, in this case, imaging of the behavior of cells within the cell sorting structure. Such optically-transparent electrode layers may allow for optically-based analysis techniques to be used to analyze cells or other materials that may be concentrated within DEP concentration zones of a three-dimensional cell sorter or particulate sorter. As can be seen in FIG. 6C, the application of AC voltage to the electrode layers has caused the first cell visible in FIG. 6B to migrate in the z-direction and into the passage corresponding with the focal plane. A second cell, further upstream from the first cell, is also barely visible in the passage in FIG. 6C.

In FIG. 6D, the DEP effect caused by the application of AC voltage across the electrode layers has caused both the first cell and the second cell to move into the passage corresponding with the focal plane, allowing for sharp imaging of both cells. In some implementations, a combination of such z-separation and proper focal plane alignment may allow for target cells to be separated from a fluid sample within a DEP separation region and optically processed, e.g., counted using a machine vision system, without actually mechanically separating the collection stream from the waste stream of the three-dimensional DEP cell sorter. In other implementations, however, actual separation of the sorted cells from the waste stream in the post-DEP separation region may still occur, allowing such separated cells to be routed to subsequent chambers for analysis where the presence of other cell material may be undesirable.

Three-dimensional DEP cell sorters such as those discussed herein may exhibit performance that is a significant improvement over "tilted electrode" DEP cell sorters such as those depicted in FIGS. 1 and 2. For example, tilted electrode designs typically feature DEP interaction distances that are limited to the length of the electrode patterns, which are typically limited to several hundred µm in length, whereas three-dimensional DEP cell sorters such as those described herein may have DEP interaction distances that span across an entire microfluidic chip (currently, microfluidic chips have a typical size of 10 cm by 10 cm), and thus may have DEP interaction distances of 10 cm or longer, which is 3 orders of magnitude greater than the fastest tilted-electrode DEP sorters currently available.

Due to the dependence of the three-dimensional DEP sorting effect on fluid passage cross-section geometry, DEP sorting due to a particular cross-sectional passage shape may occur along such a passage or passages for as long as the cross-sectional passage shape exists. Thus, three-dimensional DEP sorting may occur in a passage or passages across the entire span of a microfluidic chip, e.g., approximately 10 cm (for a passage parallel to the chip edge) or 14 cm (for a passage on the chip diagonal) on a 10 cm-square chip. Moreover, three-dimensional DEP sorting structures may also be implemented in non-linear patterns, e.g., the passages in which three-dimensional DEP sorting occurs may be routed to as to turn corners or loop back on themselves (similar to the U-turn shown in FIG. 9(d)) to form a serpentine passage. Using such non-linear patterns, a passage for a three-dimensional DEP cell sorter on a 10cm-square microfluidic chip may reach up to 1 m to 10 m in length.

While various materials may be used for the electrically-insulating layer, one common material used in microfluidic devices is PDMS. PDMS is an optically clear, elastomeric material that can be flowed onto a mold, cured, and then removed. PDMS is particularly well-suited to reproducing small-scale, e.g., nano- or micro-scale, features such as microfluidic channels, ports, etc. Currently, existing manufacturing methods for PDMS structures focus on forming individual PDMS layers including various microfluidic features and then bonding them to each other to produce a multi-layer stack, each layer having a different set of features. Such techniques allow for multiple separate fluid flow passages to exist within a single multi-layer PDMS stack. However, current production techniques typically have issues reliably producing through-layer vias to allow passages on different layers to fluidly communicate with one another. Specifically, the present inventors have realized that current production techniques may produce edge ridges around such vias. In the context of a large, linear or curvilinear via, e.g., such as that formed by the second passage 330 between the first passage 326 and the third passage 328, such ridges may interfere with inter-layer bonding and may also cause undesirable interference with the generation of the electromagnetic field within the sample fluid. Since many PDMS structures are manufactured using a multi-layered approach, such edge ridges may appear on multiple layers and, in aggregate, result in large non-uniformities in the overall thickness of the PDMS structure, which is generally undesirable. Other materials that may be suitable for use in the electrically-insulating layer may include silicon dioxide, silicon nitride, and amorphous, poly-, and single-crystalline silicon, as well as other electrically-insulating materials. Thus, while PDMS may be well-suited for forming three-dimensional DEP cell sorter electrically-insulating layers, other materials may also be used.

Given the suitability of PDMS for producing the above-discussed three-dimensional DEP cell sorter structures, the present inventors conceived of a new manufacturing technique for multi-layer PDMS structures that allows for through-via features with reduced, or eliminated, edge-ridges. This technique may be used to produce cell sorters as detailed herein, but may also be used to produce any number of other PDMS multi-layer structures. It may be especially useful in producing multi-layer PDMS structures requiring through-via structures. The technique may also be used, with appropriate modification, to produce layer structures from elastomeric materials other than PDMS.

It is to be understood that three-dimensional DEP cell sorters as discussed herein may also be made using techniques other than those discussed in detail herein. For example, a three-dimensional DEP cell sorter may be made using plastic molding to create channel or passage structures and laser drilling to create interlayer vias, e.g., to join the passages together in the z-direction within the DEP separation region.

FIGS. 5A through 5ZB depict, via simplified cross-sectional views, various stages of a manufacturing technique for producing multi-layer PDMS structures. The structure that is being constructed in FIGS. 5A through 5ZB is a portion of a three-dimensional DEP cell sorter, e.g., the features within the DEP separation region of such a cell sorter. FIGS. 5A through 5ZB are not drawn to scale. In FIGS. 5A through 5P, the Figures depict two different manufacturing streams—the steps in the streams may be largely the same, but the molds used may have different feature sizes. For example, the cross-sections on the left side of each Figure depict the formation of a PDMS layer that may be used to provide the first passage or the third passage of a cell sorter, and the cross-sections on the right side of each Figure may depict the formation of a PDMS layer that may be used to provide the second passage of the cell sorter. FIGS. 5Q through 5ZB depict the assembly of the layers into an assembled cell sorter.

Figure 7A:
FIGS. 7A through 7ZB depict, via simplified cross-sectional views, various stages of a manufacturing technique for producing multi-layer PDMS structures.
Figure 7A:
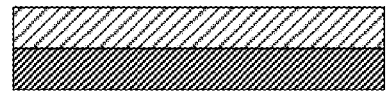
Figure 7B:
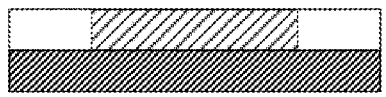
Figure 7B:
Figure 7C:
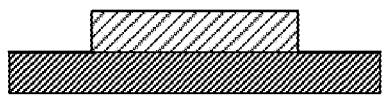
Figure 7C:
Figure 7D:
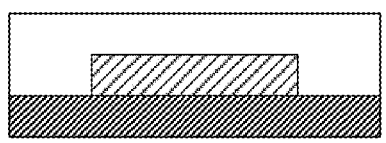
Figure 7D:
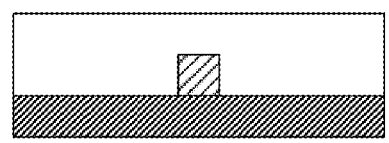
Figure 7E:
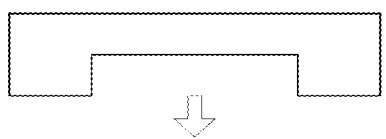
Figure 7E:
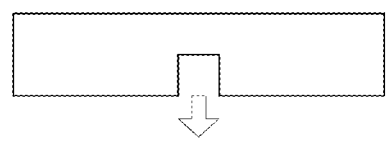
Figure 7E:
Figure 7E:
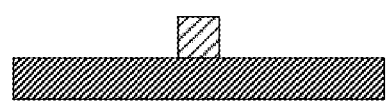
Figure 7F:

In FIG. 7A, a hard substrate may be prepared for etching by depositing or providing a photo-patternable or photo-resistive material on the substrate, such a material may be, for example, negative photoresist SU8 or positive photoresist AZ4620, and the substrate may, for example, be silicon or glass, although other photoresists or photo-patternable materials may be used as well, as well as other substrate materials. In FIG. 7B, an etching operation may remove material from the hard substrate to form a hard master mold. Alternatively, the raised features on the hard master molds may be formed by deposition instead of etching. In FIG. 7C, the hard master mold is coated with a conformal silane surface treatment to facilitate later removal of cured PDMS from the hard master mold. In FIG. 7D, uncured PDMS may be poured onto the hard master mold and cured to form a complementary PDMS mold. In FIG. 7E, the PDMS mold may then be separated from the hard master mold. In FIG. 7F, the PDMS mold may be coated with a conformal silane surface treatment.

Figure 7G:
Figure 7H:
Figure 7I:
Figure 7J:
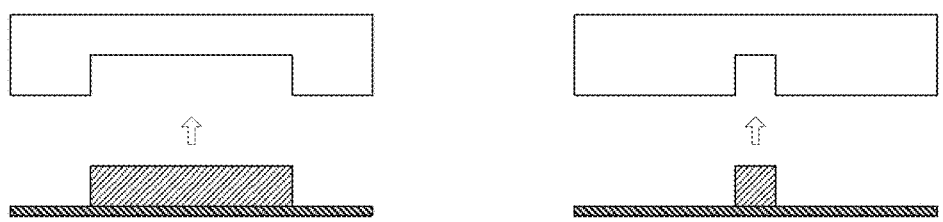

In FIG. 7G, the PDMS mold may be temporarily set aside and another hard substrate, e.g., silicon or glass, may be prepared by pouring uncured PDMS onto the hard substrate. In FIG. 7H, the PDMS mold may be retrieved, and in FIG. 7I, the PDMS mold may be pressed into the uncured PDMS on the substrate and the uncured PDMS may then be cured. In FIG. 7J, the PDMS mold may be removed from the cured PDMS on the substrate. The resulting PDMS structure on the substrate may be an exact, or near-exact, duplicate of the hard master mold and may be referred to herein as the PDMS master mold. In some implementations of the method, the PDMS master mold fabrication may be skipped, and the hard master mold may be used in place of the PDMS master mold in the steps below. A hard master mold may be more suited to large-scale production runs since such master molds are more robust than PDMS master molds. A PDMS master mold may be used for low-scale production runs or for laboratory testing where higher feature quality may be desired.

Figure 7K:

In FIG. 7K, the PDMS master mold may be coated with a CYTOP™ surface treatment to assist in later removal of cast PDMS parts.

Figure 7L:
Figure 7M:
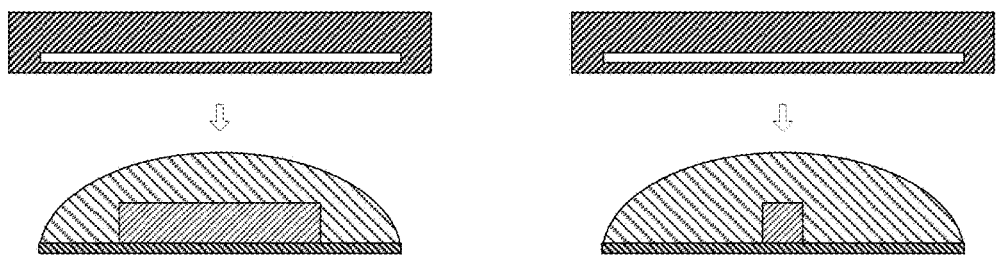

In FIG. 7L, uncured PDMS may be applied to the PDMS master mold. In FIG. 7M, a hybrid stamping is used to compress the uncured PDMS against the PDMS master mold. A hybrid stamping may include a plate of material with a much higher modulus than PDMS, e.g., is much stiffer than PDMS; the plate may have a thin layer of PDMS on at least one side. For example, the plate may have a plastic plate with a Young's modulus of 3.2 GPa and be covered with a 30 μm layer of PDMS (Young's modulus of 0.0006 GPa) on one side. The plate may be located such that a very thin layer of PDMS exists between the plate and the uncured PDMS and the PDMS master mold. This thin layer may be, for example, on the order of 500 microns or less in thickness. In practice, thicknesses of 10 to 30 microns have been found to work well. The plate may be plastic, glass, or other material with a substantially higher modulus than that of PDMS. In practice, plastic plates proved to be more robust than glass plates. The plate may act as an intermediate load spreader within the PDMS stamping to distribute a compression load across the PDMS master mold and the uncured PDMS. The thin layer of PDMS may allow for very small localized deflections that allow for full contact between the PDMS mold and the stamping, thus ensuring clear via formation, while avoiding the creation of large edge ridges that appear when a non-hybrid stamping is used.

The embedded-plate stamping shown may be provided by spin-coating the plate with PDMS. However, it was discovered that PDMS exhibits inconsistent curing behavior when applied in too thin a layer—the PDMS will frequently not set at thicknesses such as those discussed above and remains in a liquid state, resulting in an unreliable manufacturing technique. It was a surprising discovery, however, to learn that adding a platinum catalyst to the PDMS can cause a thin PDMS layer to set reliably regardless of thickness. While catalysts have been used to accelerate cure rate it is believed that such catalysts have not been used to reverse a non-cure or inconsistent cure situation. Thus, the technique may include preparing a stamping (this step is not shown) by coating a substantially rigid plate with a thin layer of PDMS with a platinum catalyst added. The stamping may also have a thicker layer of PDMS on the opposite side of the plate to allow for easy handling or integration with existing equipment, although such a thicker layer is not strictly necessary. The thin layer of PDMS (or the entire PDMS stamping) may be treated with a silane surface treatment, e.g., trichloro (1H,1H,2H,2H-perfluorooctyl)silane (also referred to as "PFOCTS"). Such PFOCTS treatment may be carried out via an evaporation process within a closed chamber.

The platinum catalyst may, for example, be platinum-divinyltetramethyldisiloxane ($C_8H_{18}OPtSi_2$), which is typically used as in ingredient in hard PDMS (the PDMS discussed herein is soft PDMS, and remains soft PDMS even after the platinum catalyst is added). The platinum catalyst may be added in addition to any normally-applied curing agent, although the amount of platinum catalyst that may be applied may be very slight. For example, in some implementations, between 16 to 20 μL of platinum-divinyltetramethyldisiloxane ($C_8H_{18}OPtSi_2$) may be added per 10 g of PDMS base and 1 g of PDMS curing agent. Of course, in the future, manufacturers may begin adding such a catalyst to existing curing agents to eliminate the need to add the catalyst separately, so it is to be understood that the above ratio is with reference to standard PDMS curing agents in existence at the time of this filing. A later-offered curing agent that has a composition similar to existing curing agents and also having a platinum-divinyltetramethyldisiloxane ($C_8H_{18}OPtSi_2$) present in approximately the same ratio. For example, a curing agent has a mass fraction of platinum-divinyltetramethyldisiloxane of approximately 1% to 2.5%, then this would be substantially equivalent to the separately-added catalyst described above.

In some implementations, if a PDMS master mold is used, the hybrid stamping may be replaced by a hard stamping, e.g., a plate of glass or hard plastic. In such implementations, the PDMS master mold may deflect slightly to allow for a tight mechanical interface between the PDMS master mold and the stamping, thus allowing the creation of clean vias.

Figure 7N:
Figure 7O:
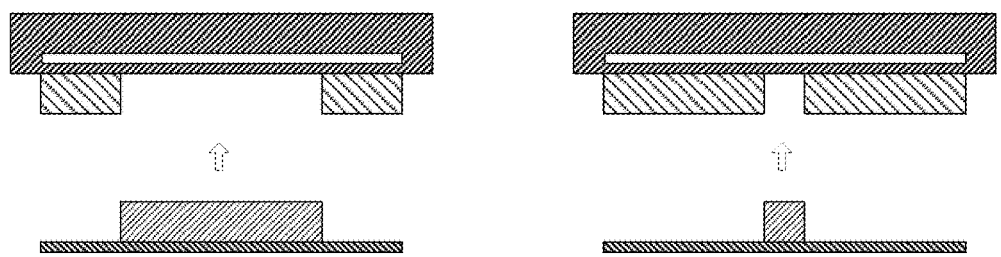

In FIG. 7N, the stamping has been compressed against the uncured PDMS and the PDMS master mold and the uncured PDMS then cured. In FIG. 7O, the cured PDMS layer is removed from the PDMS master mold by pulling the stamping away from the PDMS master mold. Due to the higher bond strength in silane-treated surfaces as compared with CYTOP-treated surfaces, the PDMS layer will stay bonded to the stamping, allowing for easy transfer to other structures.

Figure 7P:
Figure 7Q:
Figure 7R:
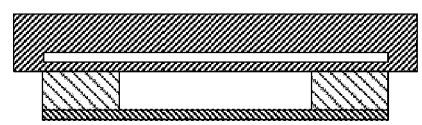
Figure 7S:
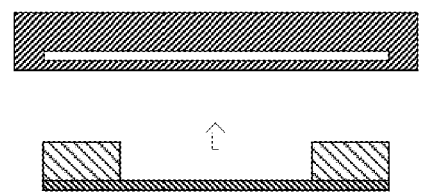

FIG. 7P depicts the removed PDMS layer bonded to the stamping; the PDMS layer may be treated with an oxygen plasma to facilitate later bonding with a glass or PDMS structure. In FIG. 7Q, one of the PDMS layers is positioned over a prepared glass substrate; the glass substrate may, for example, be prepared by coating it with an electrically-conductive coating such as ITO so that it may act as an electrode layer of a DEP cell sorter. In FIG. 7R, the PDMS layer may be directly bonded to the glass substrate as a result of the oxygen plasma treatment of the PDMS layer. In FIG. 7S, the stamping may be removed—due to the higher bond strength of the direct bonding via oxygen plasma treatment as compared with the bond across the silane-treated surfaces, the PDMS layer may separate from the stamping and remain cleanly attached to the glass substrate. The PDMS layer placed on the substrate in this case corresponds to a sublayer of an electrically-insulating layer in a DEP cell sorter having a first or third passage in it.

Figure 7T:
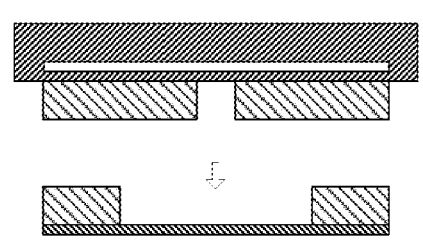
Figure 7U:
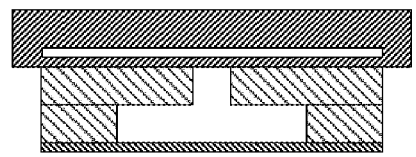
Figure 7V:
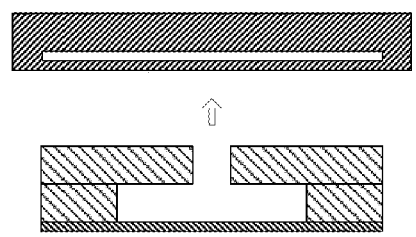

In FIG. 7T, another PDMS layer, this time corresponding with a sublayer of an electrically-insulating layer in a DEP cell sorter having a second passage in it, may be positioned over the previously-placed PDMS layer using the stamping to which it is attached. This second PDMS layer may also be treated with an oxygen plasma to facilitate direct covalent bonding to the previously-placed PDMS layer. In FIG. 7U, the second PDMS layer may be directly bonded to the first PDMS layer by compressing it into the first PDMS layer with the stamping. In FIG. 7V, the stamping may be removed in much the same manner as in FIG. 7S.

Figure 7W:
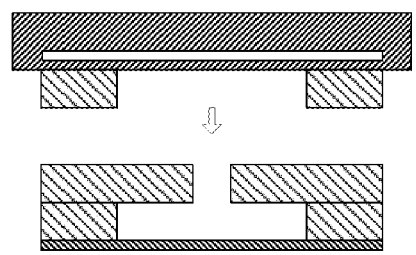
Figure 7X:
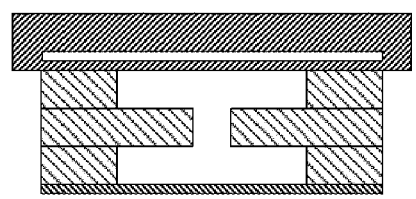
Figure 7Y:
Figure 7Y:
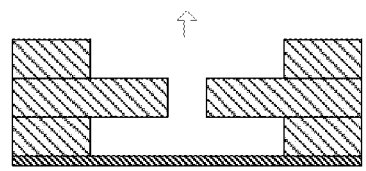
Figure 7Z:
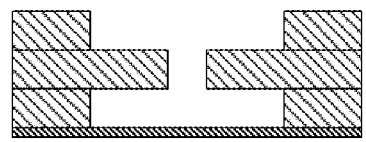
Figure 7Z:
Figure 7Z:
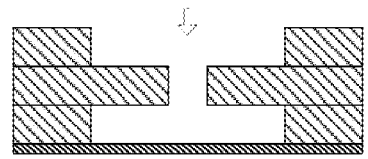
Figure 7Z:
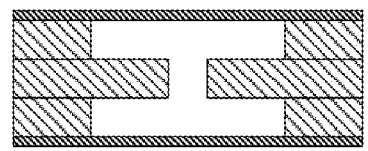

In FIG. 7W, a third PDMS layer, in this case similar to the first PDMS layer, may be positioned over the first and second PDMS layers. The third PDMS layer, as with the other PDMS layers, may be treated with an oxygen plasma. In FIG. 7X, the third PDMS layer may be directly bonded to the second PDMS layer to form a three-layer stack of PDMS layers that are fused into one, essentially contiguous, structure. In FIG. 7Y, the stamping may be removed, leaving the 3-layer PDMS structure behind. In FIG. 7Z, the exposed top of the PDMS structure may be prepared for bonding to another hard substrate, e.g., glass. In FIG. 7ZA, the hard substrate may be positioned over the assembled PDMS stack, and in FIG. 7ZB, the hard substrate may be bonded to the stack.

For each PDMS layer that is bonded using direct bonding via oxygen plasma treatment, the direct covalent bonds formed at the oxygen plasma-treated surface may be substantially stronger than the bond between the hybrid stamping and the PDMS layer, allowing the hybrid stamping to be removed from the PDMS layer and re-used after the PDMS layer is bonded at the oxygen plasma-treated surface.

Figure 8:
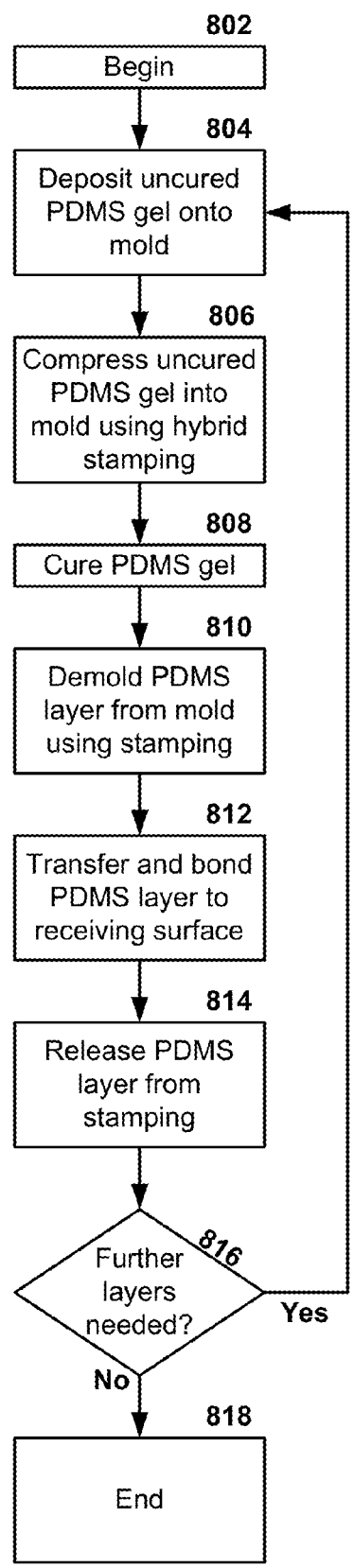
FIG. 8 depicts a flow chart summarizing a PDMS layer fabrication technique.

FIG. 8 depicts a flow chart summarizing the above technique at a high level. In block 802, the technique may begin. In block 804, uncured PDMS gel may be poured or deposited onto a mold. In block 806, the uncured PDMS gel may be pressed into the mold using a hybrid stamping. It is to be understood that if a PDMS mold is used, the hybrid stamping may be replaced with a hard stamping, e.g., a flat plastic plate. In block 808, the compressed uncured PDMS gel may be cured. After curing, the resulting cured PDMS layer may be demolded from the mold in block 810 using the stamping. In block 812, the cured PDMS layer may be transferred to a receiving surface, e.g., a glass or plastic substrate or a previously-applied PDMS layer, and bonded to the receiving surface. In block 814, the PDMS layer may be released from the stamping and the stamping may then be re-used in another molding process. In block 816, a decision may be made as to whether further PDMS layers are desired. If so, then the technique may return to block 804 (although different molds may be used as needed). In not, then the technique may proceed to block 818. It is to be understood that the above technique may be augmented by additional activities (not shown) that may be interspersed between various activities shown in FIG. 8. Additionally, other activities may precede or follow blocks 802 and 818, i.e., the technique is not limited to only the activities listed.

The resulting structure from techniques such as those outlined above with respect to FIGS. 7A through 7ZB and FIG. 8 may provide very clean inter-layer via features, and may thus be particularly well-suited for microfluidic devices feature such vias, e.g., a DEP cell sorter as discussed above with respect to FIGS. 3A through 3D. The above technique may be modified as needed to omit certain steps, add other steps, and otherwise tailor the technique for particular design requirements. For example, it may be possible to form features with stepped cross-sections in the molds, thus reducing the number of individual layers that must be made and bonded together. While the depicted technique was shown for a 3-layer stack of PDMS layers, more or less PDMS layers may be manufacturing in this manner and assembled into a PDMS layer stack. This manufacturing technique may be used for a variety of other PDMS structures besides three-dimensional DEP cell sorter structures, e.g., microfluidic structures having high aspect-ratio features.

Figure 9:
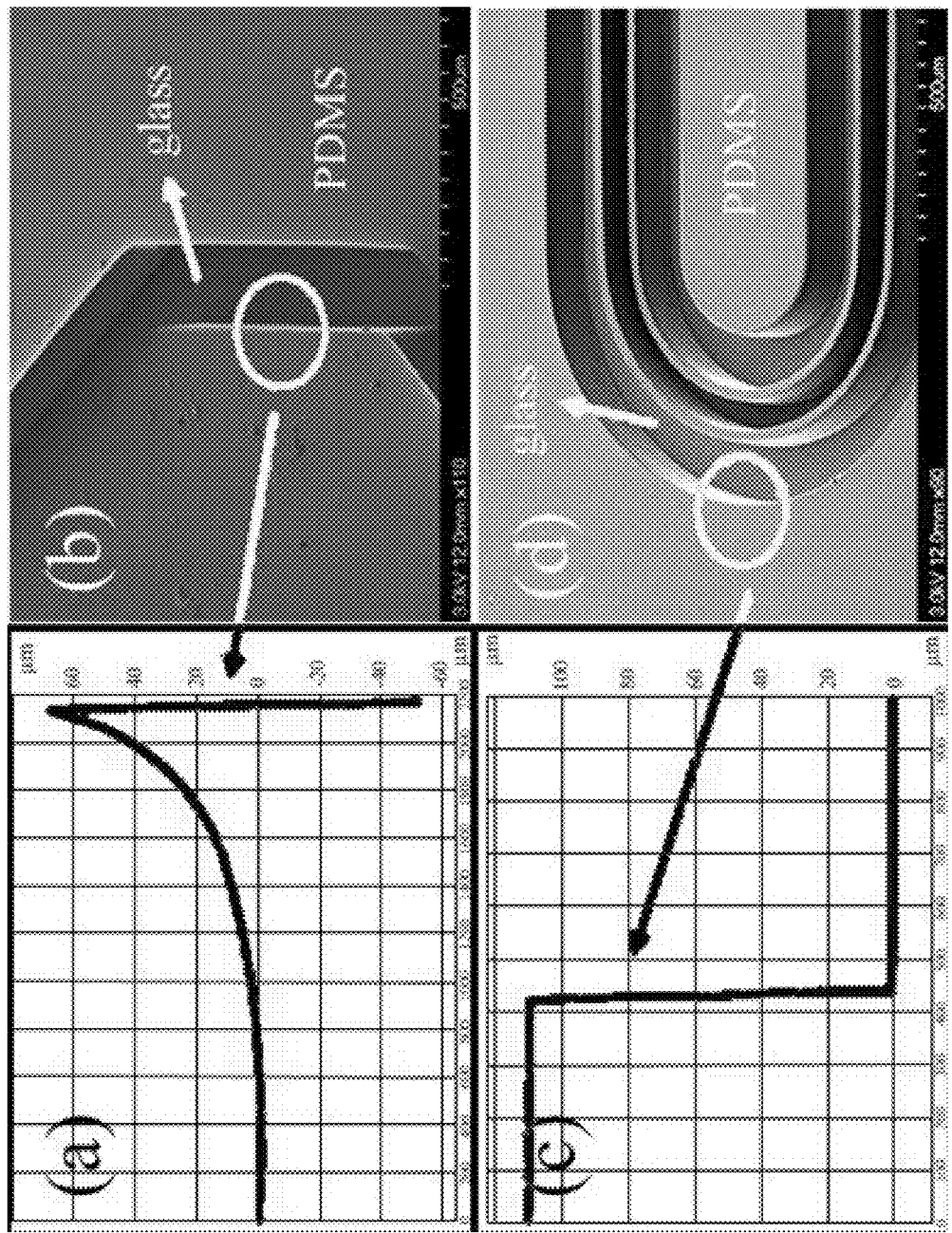
FIG. 9 depicts two examples of molded microfluidic features and the edge ridges, or lack thereof, formed using two different manufacturing processes.

FIG. 9 depicts two examples of molded microfluidic features and the edge ridges, or lack thereof, formed using two different manufacturing processes. In the upper half of FIG. 9, an image of a channel or passage produced using a non-hybrid stamping, i.e., a large-thickness, solid PDMS stamping, is on the right (b), and a plot of the edge profile at the circled location in (b) is shown on the left in (a). As can be seen, there is a 60 μm edge ridge present.

In the lower half of FIG. 9, an image of a channel or passage made using a hybrid stamping, as discussed herein, is shown on the right (d), and a plot of the edge profile at the circled location in (d) is shown on the left in (c). As can be seen, there is no discernible edge ridge present.

It is to be understood that while the discussion herein of three-dimensional DEP cell sorter structures has focused primarily on structures where the electrically-insulating layer is sandwiched between discrete electrode layers, in some implementations of three-dimensional DEP cell sorters, portions of the electrically-insulating layer may be formed directly on the electrode layers. For example, in some implementations, sub-layers of the electrically-insulating layer may be formed by materials deposited directly on the electrode layers using a patterned deposition or removed from an electrically-insulating layer deposited on the electrode layers using an etching technique. The patterning may include passages that partially form a three-dimensional DEP cell sorter. Another sub-layer of electrically-insulating material, e.g., a PDMS sub-layer, may then be sandwiched between the electrode layers with the patterned, electrically-insulating sub-layers. The aggregate electrically-insulating structure may thus include the PDMS sub-layer, as well as the electrically-insulating sub-layers formed directly on the electrode layers. Electrically-insulating sub-layers that are formed directly on the electrode layers may, for example, be more than 2 μm thick.

While various implementations have been described herein, it should be understood that they have been presented by way of example only, and not limitation. Thus, the breadth and scope of the present disclosure should not be limited by any of the implementations described herein, but should be defined only in accordance with the following and later-submitted claims and their equivalents.

It will be understood that unless features in any of the above-described implementations are expressly identified as incompatible with one another or the surrounding context implies that they are mutually exclusive and not readily combinable in a complementary and/or supportive sense, the totality of this disclosure contemplates and envisions that specific features of those implementations can be selectively combined to provide one or more comprehensive, but slightly different, technical solutions. It will therefore be further appreciated that the above description has been given by way of example only and that modifications in detail may be made within the scope of the disclosure.

What is claimed is:

1. A 3-dimensional dielectrophoretic (DEP) sorting device, the device comprising:
   a first electrode;
   a second electrode; and
   an electrically-insulating layer sandwiched between the first electrode and the second electrode, wherein:
   the electrically-insulating layer includes a separation passage with walls partially bounded by the first electrode and the second electrode,
   the electrically-insulating layer includes a collection passage smaller than the separation passage in cross-sectional thickness and located at an inter-electrode location between the first electrode and the second electrode,
   the separation passage is shaped to produce an electromagnetic field that causes a dielectrophoretic effect to draw responsive cells or particulates to a location between the first electrode and the second electrode that substantially corresponds with the inter-electrode location of the collection passage, and
   the collection passage and the separation passage are configured such that cells or particulates drawn to the inter-electrode location between the first electrode and the second electrode in the separation passage are then flowed into the collection passage.

2. A 3-dimensional dielectrophoretic (DEP) sorting device, the device comprising:
   a first electrode;
   a second electrode; and
   an electrically-insulating layer sandwiched between the first electrode and the second electrode, wherein:
   the electrically-insulating layer includes:
   a fluid flow passage, the fluid flow passage having a cross-section partially defined by the first electrode and the second electrode;
   a first side passage that is parallel to the fluid flow passage within a DEP-separation region of the device and separated from the fluid flow passage by a first thin, deformable wall; and a second side passage that is parallel to the fluid flow passage within the DEP-separation region and separated from the fluid flow passage by a second thin, deformable wall, wherein:

the first side passage and the second side passage are hermetically sealed from the fluid flow passage, and application of pressurized gas or fluid to the first side passage and the second side passage causes the first thin, deformable wall and the second thin, deformable wall to bulge into the fluid flow passage.

3. A 3-dimensional dielectrophoretic (DEP) sorting device, the device comprising:

a first electrode layer;

a second electrode layer;

an electrically-insulating layer interposed between the first electrode layer and the second electrode layer and having a first sub-layer and a second sub-layer;

a first passage located in the first sub-layer; and a second passage located in the second sub-layer; wherein:

the first electrode layer, the second electrode layer, and the electrically-insulating layer form a substantially planar assembly, the first electrode layer is on an opposite side of the first sub-layer from the second sub-layer, the second electrode layer is on an opposite side of the second sub-layer from the first sub-layer, the first passage and the second passage follow a common path within a DEP-separation region of the electrically-insulating layer and are in direct fluid communication with one another within the DEP-separation region, the first passage and the second passage each have a different cross-sectional width perpendicular to the common path and perpendicular to a normal of the substantially planar assembly, and the first passage diverges from the second passage in a post-DEP-separation region, the post-DEP-separation region located downstream of the DEP-separation region.

4. The 3-dimensional DEP sorting device of claim 3, further comprising:

a third sub-layer of the electrically-insulating layer; and a third passage located in the third sub-layer, wherein:

the second sub-layer is interposed between the first sub-layer and the third sub-layer, the third sub-layer is interposed between the second sub-layer and the second electrode layer, the third passage follows the common path within the DEP-separation region and is in direct fluid communication with the second passage within the DEP-separation region, the third passage has a cross-sectional width perpendicular to the common path and perpendicular to the normal of the substantially planar assembly that is different from the cross-sectional width of the second passage, and the third passage diverges from the second passage in the post-DEP-separation region.

5. The 3-dimensional DEP sorting device of claim 4, wherein the cross-sectional width of the second passage is less than the cross-sectional widths of the first passage and the third passage.

6. The 3-dimensional DEP sorting device of claim 4, wherein the cross-sectional width of the second passage is greater than the cross-sectional widths of the first passage and the third passage.

7. The 3-dimensional DEP sorting device of claim 3, wherein the first electrode layer and the second electrode layer are substantially flat plates with electrically-conductive surfaces facing the electrically-insulating layer.

8. The 3-dimensional DEP sorting device of claim 7, wherein the electrically-conductive surfaces extend across substantially all of the electrically-insulating layer.

9. The 3-dimensional DEP sorting device of claim 7, wherein the electrically-conductive surfaces are substantially uniform in a region bounded by the DEP-separation region and sidewalls of the first passage or a region bounded by the DEP-separation region and sidewalls of the second passage.

10. The 3-dimensional DEP sorting device of claim 7, wherein one or both of the electrically-conductive surfaces is coated with an electrically non-conductive coating less than 2 μm in thickness.

11. The 3-dimensional DEP sorting device of claim 3, wherein the electrically-insulating layer is a polydimethylsiloxane (PDMS) structure.

12. The 3-dimensional DEP sorting device of claim 3, wherein the first sub-layer has a thickness of approximately 1 μm to 100 μm and the second sub-layer has a thickness of approximately 10 μm to 100 μm.

13. The 3-dimensional DEP sorting device of claim 3, wherein the first sub-layer has a thickness of approximately 100 μm to 500 μm and the second sub-layer has a thickness of approximately 100 μm to 500 μm.

14. The 3-dimensional DEP sorting device of claim 3, wherein the first passage has a cross-sectional width of at least 1 μm and the second passage has a cross-sectional width of at least 2 μm.

15. The 3-dimensional DEP sorting device of claim 3, wherein the first passage has a cross-sectional width of less than 1 μm and the second passage has a cross-sectional width of less than 2 μm.

16. The 3-dimensional DEP sorting device of claim 3, wherein application of an alternating-current (AC) voltage across the first electrode layer and the second electrode layer causes a non-uniform electromagnetic field to develop within a fluid flowed through the first passage and the second passage within the DEP-separation region, wherein the non-uniform electromagnetic field has an intensity that is biased towards one of the first passage or the second passage.

17. The 3-dimensional DEP sorting device of claim 3, further comprising one or more additional passages, each located in an additional sub-layer, wherein:

the one or more additional passages includes a third passage, the one or more additional passages follow the common path within the DEP-separation region of the electrically-insulating layer and are in direct fluid communication with one another and the first passage and the second passage within the DEP-separation region, the one or more additional passages each have a cross-sectional width perpendicular to the common path and perpendicular to the normal of the substantially planar assembly, the cross-sectional width of each particular additional passage is different from the cross-sectional width of each additional passage neighboring that particular additional passage, and at least one of the one or more additional passages diverges from the second passage in the post-DEP-separation region.

18. The 3-dimensional DEP sorting device of claim 3, wherein the first electrode layer and the second electrode layer include patterned electrodes in the DEP-separation region.

19. The 3-dimensional DEP sorting device of claim 3, wherein the electrically-insulating layer is a polydimethylsiloxane (PDMS) structure formed by bonding multiple individual PDMS layers together.

20. The 3-dimensional DEP sorting device of claim 19, wherein:
the first sub-layer is formed by one or more of the individual PDMS layers, and
the second sub-layer is formed by one or more of the individual PDMS layers.

21. The 3-dimensional DEP sorting device of claim 19, wherein the electrically-insulating layer is a composite structure that includes a combination of different materials.

22. The 3-dimensional DEP sorting device of claim 21, wherein the electrically-insulating layer is a composite structure that includes non-PDMS materials suspended in PDMS.

23. The 3-dimensional DEP sorting device of claim 3, wherein the 3-dimensional DEP sorting device is incorporated into a hand-held device.

24. The 3-dimensional DEP sorting device of claim 3, wherein the 3-dimensional DEP sorting device is coupled to a hand-actuated pumping device configured to drive a fluid sample through the first passage and the second passage of the sorting device.

25. The 3-dimensional DEP sorting device of claim 4, wherein the first passage and the third passage have different cross-sectional widths.

26. The 3-dimensional DEP sorting device of claim 4, wherein the first passage, the second passage, and the third passage have an aggregate cross-section that is substantially in the shape of a sideways "H" within the DEP-separation region, thereby causing particulates or cells with positive DEP that are entrained in a fluid to collect in the second passage when an alternating-current voltage is applied between the first electrode layer and the second electrode layer.

27. The 3-dimensional DEP sorting device of claim 4, wherein the first passage, the second passage, and the third passage have an aggregate cross-section that is substantially in the shape of a "+" within the DEP-separation region, thereby causing particulates or cells with negative DEP that are entrained in a fluid to collect in the second passage when an alternating-current voltage is applied between the first electrode layer and the second electrode layer.

28. The 3-dimensional DEP sorting device of claim 4, wherein the first passage, the second passage, and the third passage are substantially centered over one another in a direction perpendicular to the common path and parallel to the substantially planar assembly within the DEP-separation region.

* * * * *